(12) United States Patent
Sarangapani et al.

(10) Patent No.: US 10,245,392 B2
(45) Date of Patent: Apr. 2, 2019

(54) OXYGEN CONCENTRATING DEVICE, WOUND CARE APPARATUS, AND TREATMENT METHODS

(71) Applicant: NEOGENIX, LLC, Ft. Lauderdale, FL (US)

(72) Inventors: Srinivasan Sarangapani, Walpole, MA (US); Lawrence J. Cali, East Falmouth, MA (US)

(73) Assignee: NEOGENIX, LLC, Fort Lauderdale, FL (US)

( * ) Notice: Subject to any disclaimer, the term of this patent is extended or adjusted under 35 U.S.C. 154(b) by 575 days.

(21) Appl. No.: 15/050,371

(22) Filed: Feb. 22, 2016

(65) Prior Publication Data

US 2016/0166781 A1    Jun. 16, 2016

Related U.S. Application Data

(63) Continuation-in-part of application No. 14/819,640, filed on Aug. 6, 2015, now Pat. No. 9,770,369.

(60) Provisional application No. 62/204,310, filed on Aug. 12, 2015, provisional application No. 62/035,233, filed on Aug. 8, 2014.

(51) Int. Cl.
| | |
|---|---|
| *A61M 27/00* | (2006.01) |
| *A61M 13/00* | (2006.01) |
| *A61M 1/00* | (2006.01) |
| *A61M 35/00* | (2006.01) |
| *A61F 13/00* | (2006.01) |

(52) U.S. Cl.
CPC ........ *A61M 13/003* (2013.01); *A61M 1/0023* (2013.01); *A61M 1/0088* (2013.01); *A61M 35/00* (2013.01); *A61F 13/00068* (2013.01); *A61F 2013/0017* (2013.01); *A61M 1/0084* (2013.01); *A61M 2202/0208* (2013.01); *A61M 2205/6063* (2013.01)

(58) Field of Classification Search
CPC .............. A61M 13/003; A61M 1/0023; A61M 1/0088; A61M 2205/6063; A61M 1/0084; A61M 35/00; A61M 2202/0208; A61F 13/00068; A61F 2013/0017
USPC .................................................. 604/543, 540
See application file for complete search history.

(56) References Cited

U.S. PATENT DOCUMENTS

| | | | | |
|---|---|---|---|---|
| 5,788,682 | A * | 8/1998 | Maget | ............... A61F 13/00063 604/290 |
| 2009/0112170 | A1* | 4/2009 | Wells | ................ A61F 13/00068 604/290 |

(Continued)

*Primary Examiner* — Andrew J Mensh
(74) *Attorney, Agent, or Firm* — Whiteford, Taylor & Preston, LLP; Gregory M. Stone

(57) ABSTRACT

A wound care device for delivering topical oxygen therapy, negative pressure wound therapy, and a low intensity vacuum therapy for treatment of a wound. The wound care device may include an oxygen supply MEA, an oxygen consuming MEA, a vacuum pump and motor, a pressure sensor, and a power supply and electronic controls. A dressing may be connected to the wound care device for administering topical continuous oxygen therapy and simultaneous negative pressure wound therapy to a wound. A canister or exudate trap may be positioned between the dressing and the vacuum supply port of the vacuum pump to collect and store exudates from the wound. The canister may be combined with the dressing.

33 Claims, 28 Drawing Sheets

(56) References Cited

U.S. PATENT DOCUMENTS

2009/0149821 A1\* 6/2009 Scherson ............... A61H 35/00
                                                                     604/289
2010/0217177 A1\* 8/2010 Cali ..................... A61M 35/00
                                                                     604/23

\* cited by examiner

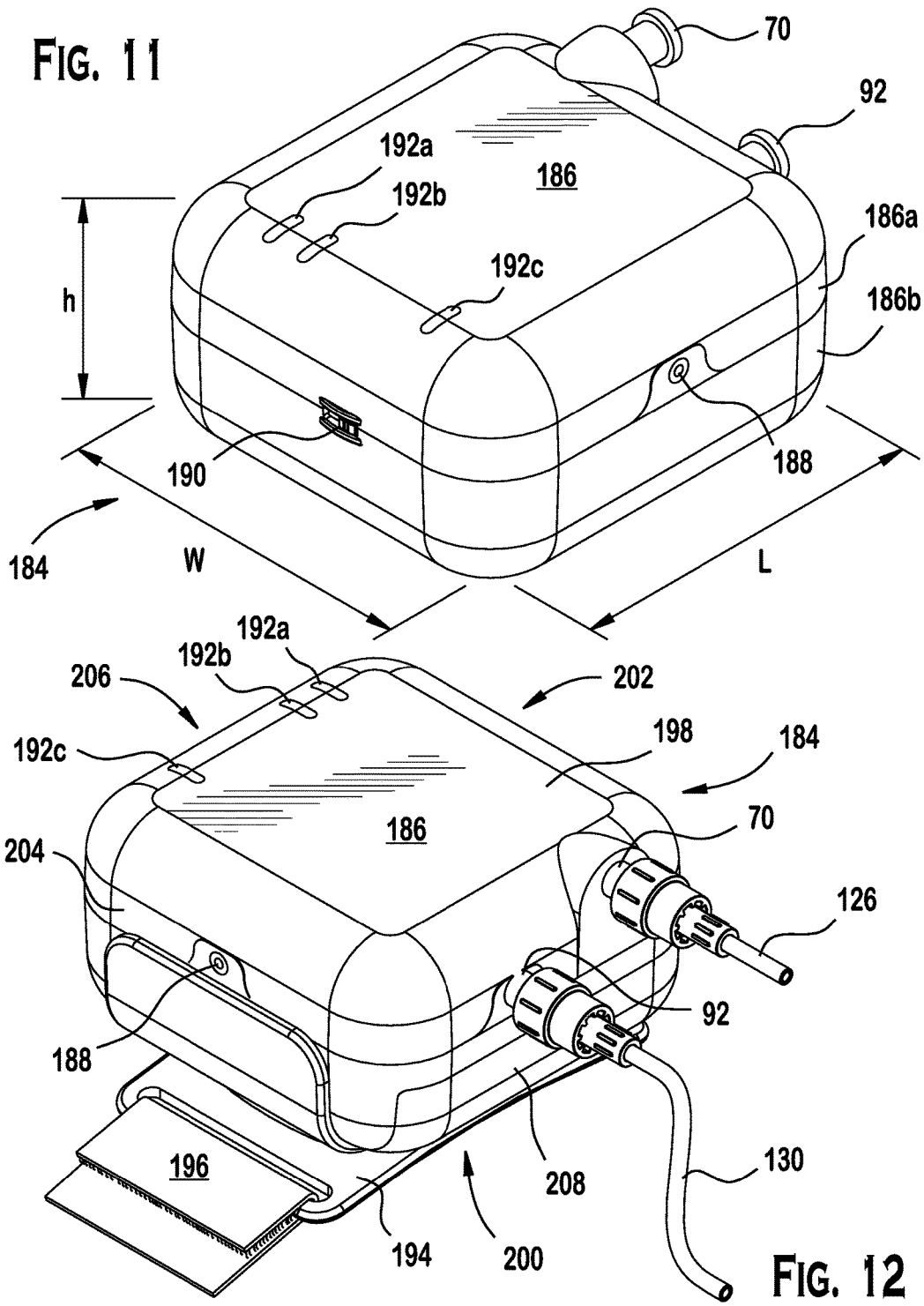

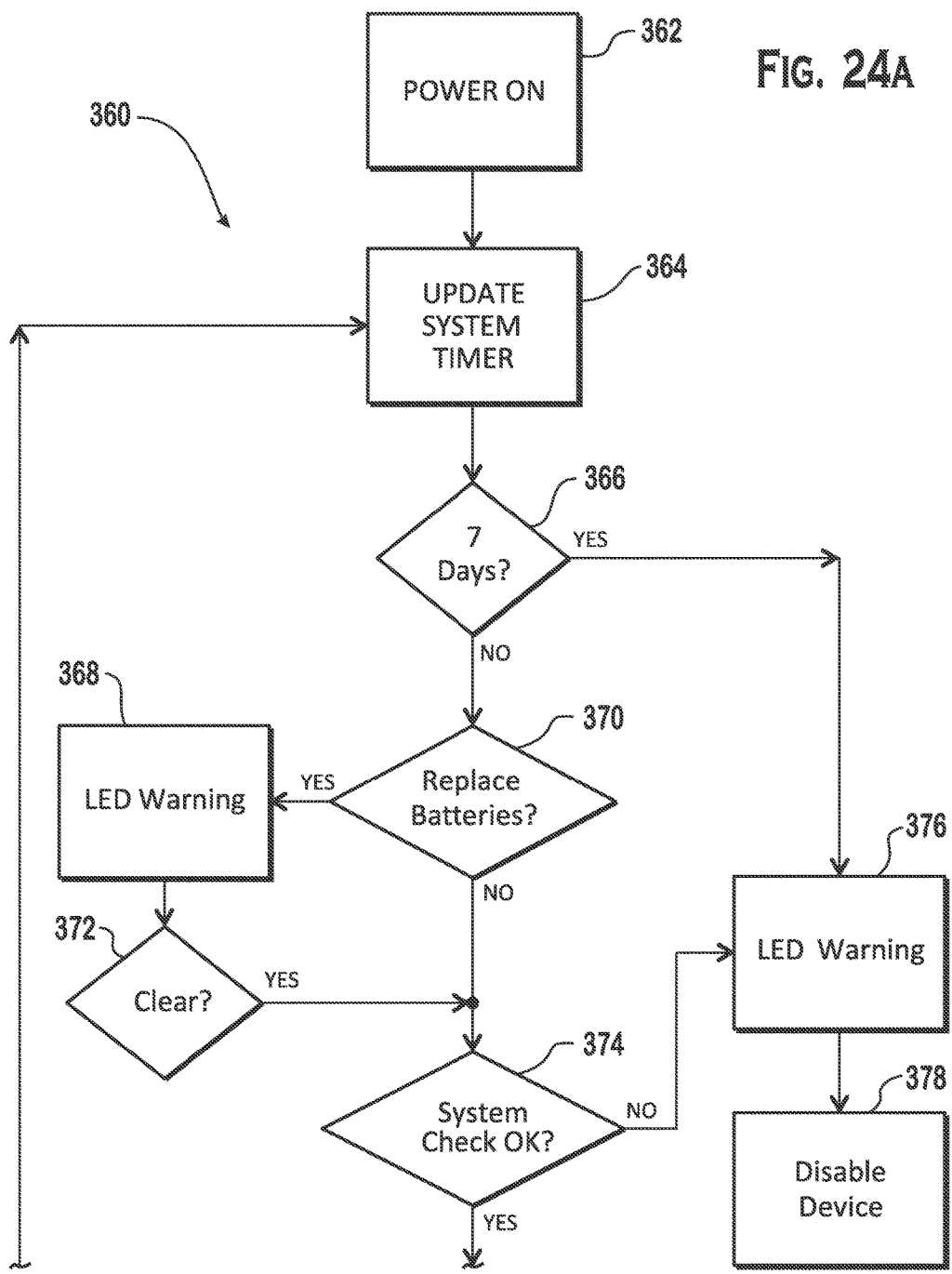

OXYGEN CONCENTRATING DEVICE, WOUND CARE APPARATUS, AND TREATMENT METHODS

CROSS REFERENCE TO RELATED APPLICATIONS

This application claims the benefit of U.S. Provisional Application No. 62/204,310, filed on Aug. 12, 2015, and also is a continuation-in-part of application Ser. No. 14/819,640, filed on Aug. 6, 2015, which claims the benefit of U.S. Provisional Application No. 62/035,233 filed on Aug. 8, 2014, the content of each of which is incorporated by reference herein in its entirety.

FIELD OF THE INVENTION

The present invention generally relates to wound care. More particularly, this invention relates to an oxygen concentrating device and apparatus for the application of negative pressure wound therapy along with transdermal oxygen delivery.

BACKGROUND

Negative Pressure Wound Therapy (NPWT) may be used to treat wounds, including acute wounds, chronic wounds, pressure ulcers, and diabetic foot ulcers. For example, a dressing may be applied to a chronic wound to form an airtight seal, and a pump may be connected via a tube to the dressing to evacuate air from the dressing and draw drainage from the wound. NPWT may accelerate wound healing by various mechanisms including: removal of exudate, reduction of edema, contraction of wound edges, stimulation of angiogenesis, changes in the wound edges, and production of granulation tissue. Nevertheless, wound treatment with NPWT may provide limited efficacy should the healing process stall or contraindications, such as advancing infection in the wound, develop. Although oxygen delivery therapies may be used to successfully treat wounds, including wounds that have failed NPWT, a need exists for new devices and systems that may improve patient outcomes and expand access to patients with limited mobility or clinical support.

SUMMARY

Hence, the present invention is directed to oxygen concentrating devices, wound care apparatuses, and methods of treating wounds. The wound care devices and apparatuses may be used to apply transdermal continuous oxygen therapy to a wound, simultaneously apply transdermal continuous oxygen therapy and negative pressure wound therapy to a wound, or to apply intermittent application of negative pressure wound therapy and transdermal oxygen to a wound.

In one embodiment, the wound care device may include an oxygen port for supplying oxygen gas for wound care, and an oxygen concentrating device fluidly connected to the oxygen port. The oxygen concentrating device may include a first membrane electrode assembly (MEA) for the production of oxygen from air. The first MEA may include a first electrode fluidly connected to a source of ambient air. The first MEA may further include a cover disposed between the first electrode and the source of ambient air. The cover may include at least one passage which fluidly connects the first electrode to the source of ambient air. The cover may restrict moisture loss from the first electrode. The first MEA may include a second electrode spaced from the first electrode, the second electrode being fluidly connected to a first basin such that the first basin is fluidly connected to the oxygen port. The first MEA may include a first ion conducting membrane positioned between the first and second electrodes. The first ion conducting membrane may include a first conductive wire connected to the first electrode, and a second conductive wire connected to the second electrode. The application of a constant electrical current through the first conductive wire and the second conductive wire may electrochemically produce oxygen on the second electrode from ambient air adjacent the first electrode, and such that when the source of ambient air has a temperature of approximately 68° F. and an ambient relative humidity which is substantially equal to or less than 30%, the voltage across the first electrode and the second electrode may increase less than 25% after 15 days of electrochemically producing oxygen on the second electrode as the result of the application of the substantially constant flow of electrical current.

The device may further include a vacuum port for providing a vacuum for wound care and a mechanical pump. The mechanical pump may include a pump intake fluidly connected to the vacuum port, and a motor for driving the mechanical pump, such that the motor may drive the mechanical pump to evacuate a gaseous mixture at a temperature ranging from approximately 60° F. to approximately 100° F. and a pressure ranging from approximately 560 mmHg absolute to approximately 760 mmHg absolute at a volumetric flow rate ranging from approximately 1 cc/min to approximately 2,500 cc/min while maintaining a vacuum at the pump intake. The vacuum may range from approximately 100 mmHg to approximately 500 mmHg. The device may include a pressure sensor fluidly connected with the vacuum port or the oxygen port.

The device may include an oxygen consuming device fluidly connected to the oxygen port. The oxygen consuming device may include a second MEA for the removal of oxygen from a gaseous mixture. The second MEA may include a third electrode fluidly connected to the first basin, a fourth electrode spaced from the third electrode, a second ion conducting membrane positioned between the third and fourth electrodes, a third conductive wire connected to the third electrode, and a fourth conductive wire connected to the fourth electrode, such that the application of a constant voltage across the third conductive wire and the fourth conductive wire electrochemically consumes oxygen from the first basin at the third electrode.

The device may include a microcontroller electrically connected to the first MEA, the second MEA, the motor, and the pressure sensor, the microcontroller being configured to regulate operation of the wound care device in a plurality of operational modes. The plurality of operational modes may include: a first operational mode in which the first MEA delivers oxygen to the oxygen port at a rate ranging from approximately 1 ml oxygen/hr to approximately 10 ml oxygen/hr at a temperature ranging from approximately 60° F. to approximately 100° F. and a pressure of approximately 760 mmHg; a second operational mode in which the second MEA consumes oxygen from the oxygen port at a rate ranging from substantially equal to or greater than 5 times the oxygen generating rate in the first operational mode; and a third operational mode in which the mechanical pump evacuates a gaseous mixture from the vacuum port at a volumetric flow rate ranging from approximately 1cc/min to approximately 2,500 cc/min while maintaining a pressure ranging from approximately 560 mmHg to approximately 680 mmHg at a wound site which is fluidly connected to the vacuum port.

The microcontroller may regulate simultaneous operation of the first operational mode and the third operational mode. The microcontroller may regulate operation of the second operational mode after regulating operation of the first operational mode.

The device may include an enclosure for housing the first MEA, the second MEA, and the mechanical pump. The enclosure may include a cover section and a base section. The first MEA and the second MEA may be secured to the cover section. The mechanical pump may be connected to the base section. The oxygen port may be connected to the cover section, and the vacuum port may be connected to the base section.

Also, the first basin may include a recess in the cover section. The device further may include a second basin adjacent the first basin. An intermediate passage may fluidly connect the first basin and the second basin. The second basin may be opposite the second MEA.

The device may include a plurality of LEDs connected to the microcontroller for signaling a status of one or more operating parameters. The device may include a replaceable power supply for operating the motor. The device may include a rechargeable power supply for operating the motor.

The pressure sensor may be fluidly connected to the vacuum port at a location between the mechanical pump and the vacuum port. The pressure sensor may be fluidly connected to the oxygen port at a location between the first MEA and the oxygen port.

The device may include a trap for storing wound care exudates, the trap being fluidly connected to the pump intake.

A passage in the cover may have a radius that is substantially equal to or greater than 0.159 mm. More than one passage may fluidly connect the first electrode to the source of ambient air. Each passage may have a cross-sectional area of approximately 0.01 cm$^2$. For example, four passages may fluidly connect the first electrode to the source of ambient air.

The present invention may be directed to an apparatus for treating a wound. In one embodiment, the apparatus may include a wound care device, and a dressing for administering treatment to a wound, the dressing comprising an oxygen delivery manifold fluidly connected to the oxygen port.

In another embodiment, an apparatus for treating a wound may include a wound care device and a dressing for administering treatment to a wound, the dressing including an oxygen delivery zone fluidly connected to the oxygen port, and a gaseous mixture and exudates removal zone fluidly connected to the vacuum port. The apparatus may include a trap for storing wound care exudates, the trap being fluidly connected to the gaseous mixture and exudates removal zone and the pump intake. The trap may be located between the pump intake and the vacuum port. The trap may be located in the dressing. The trap may include a container that is located between the vacuum port and the dressing.

The present invention may be directed to a method of treating a wound. In one embodiment, the method may include providing a wound care device; positioning a dressing over a wound for administering topical continuous oxygen therapy and negative pressure wound therapy; connecting the dressing to the wound care device; activating operation of the wound care device; supplying oxygen concentrated by the wound care device to the dressing; and applying a vacuum produced by the wound care device to the dressing. Activating operation of the wound care device may initiate a seven-day treatment cycle that comprises simultaneous topical continuous oxygen therapy and negative pressure wound therapy. Activating operation of the wound care device may initiate a seven-day treatment cycle that comprises topical continuous oxygen therapy and intermittent negative pressure wound therapy.

DESCRIPTION OF THE DRAWINGS

In the accompanying drawings, which form a part of the specification and are to be read in conjunction therewith and in which like reference numerals (or designations) are used to indicate like parts in the various views:

FIG. 11 is a perspective view of another embodiment of a wound care device in accordance with the present invention;

FIG. 12 is another perspective view of the wound care device of FIG. 11 with tubing for delivering NPWT, transdermal oxygen flow and other treatment therapies to a dressing and across a wound in accordance with the present invention;

FIG. 24A is the first of two portions of an exemplary flow diagram of a second treatment mode of the wound care device of FIG. 11;

DESCRIPTION

Figure 1:
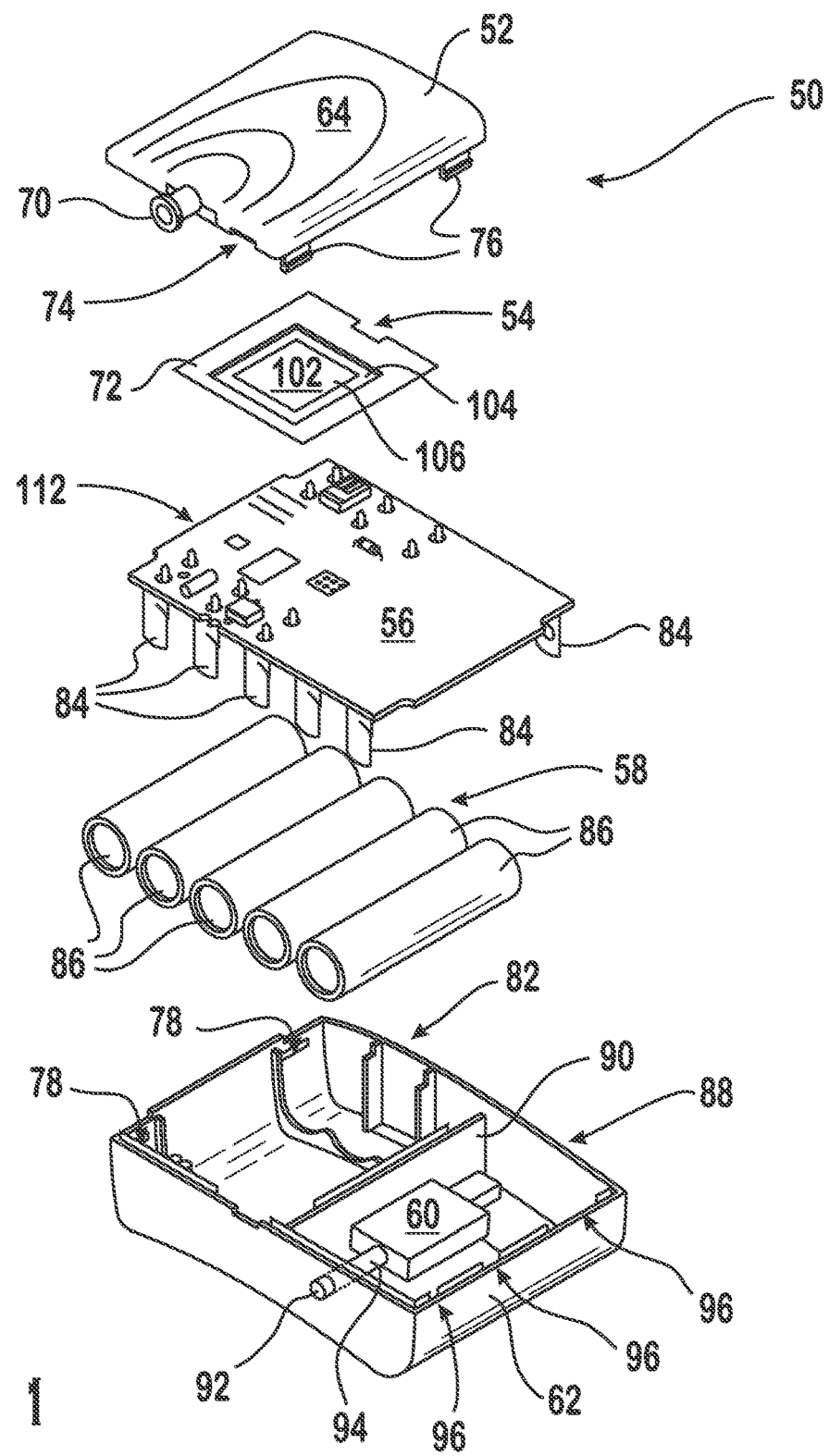
FIG. 1 is a partially exploded schematic view of an exemplary wound care device in accordance with the present invention.

FIG. 1 shows an exploded view of an exemplary embodiment of a wound care device 50 in accordance with the present invention. The wound care device 50 may include a lid (or upper housing component) 52, an oxygen concentrating device 54, a printed circuit board (PCB) 56, a battery pack 58, a vacuum pump 60, and a bottom enclosure (or lower housing component) 62.

Figure 1A:
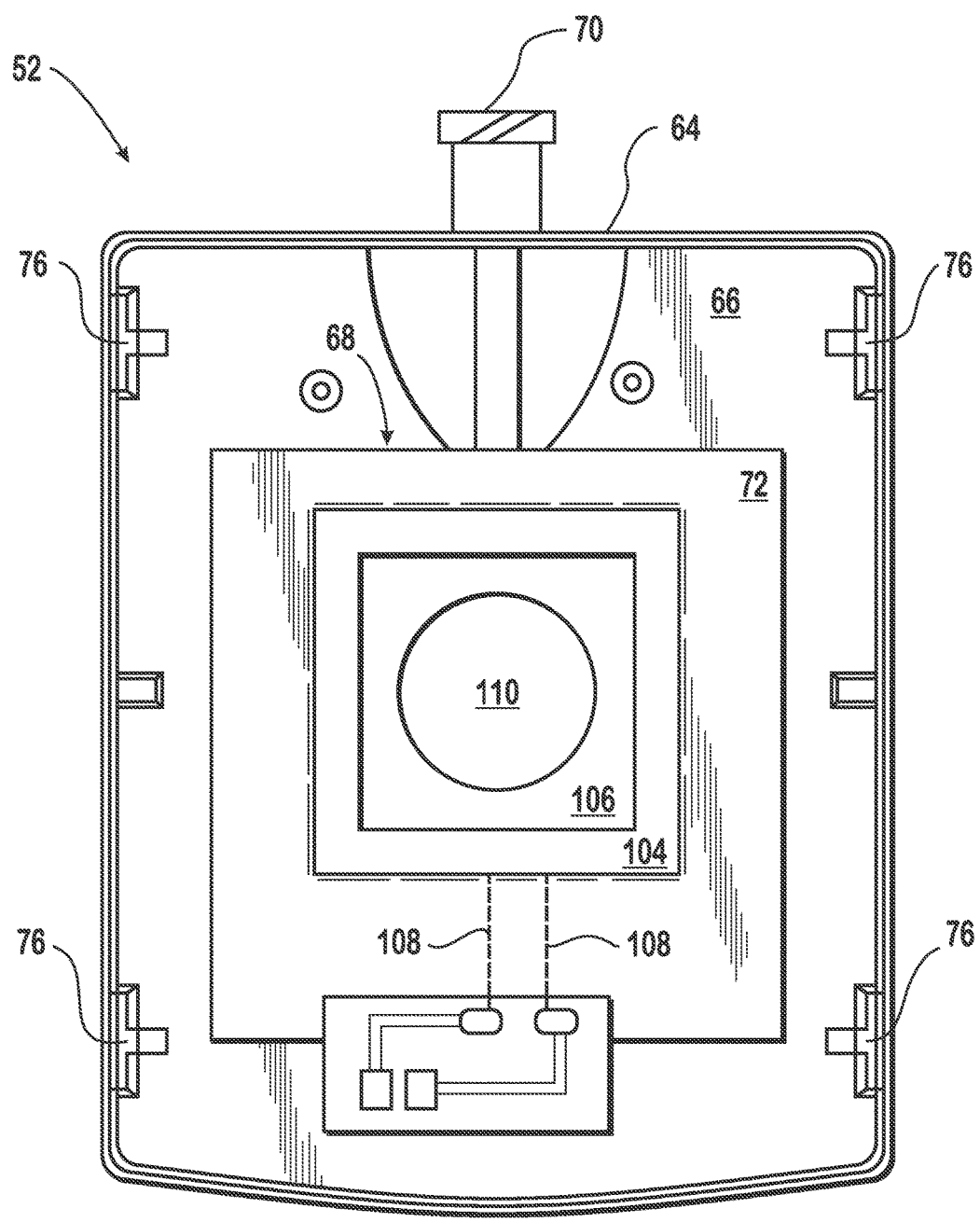
FIG. 1A is a plan view of the interior side of the lid of the wound care device of FIG. 1.

Referring to FIG. 1A, the lid 52 may include an exterior surface 64 and an interior surface 66. The interior surface 66 may include an oxygen collection chamber 68. The lid 52 further may include a tubular port 70 on an exterior side wall portion of the lid. The tubular port 70 may be in fluid communication with the oxygen collection chamber 68. The perimeter of the oxygen collection chamber may be encircled by one or more adhesive strips 72. The adhesive strip(s) 72 may provide an attachment structure for securing the oxygen concentrating device 54 to the lid. The adhesive strip(s) 72 also may cooperate with the oxygen generating device to form a gas impermeable seal between the interior surface of the lid and the oxygen concentrating device such that the oxygen collection chamber is isolated from the housing interior. Although the oxygen concentrating device shown in FIG. 1 may be disposed on the lid, the oxygen concentrating device may be associated with another part of the wound care device (e.g., an interior wall or compartment) provided that the relevant operational features of the oxygen concentrating device remain in fluid communication with an oxygen source (e.g., the ambient atmosphere).

Referring to FIG. 1, the lid 52 may include openings or notches 74 to allow for entry of air into the housing interior. In addition, the lid may include one or more projections 76 (e.g., locking tabs) which may extend from the interior surface 66. Each of the projections may mate with a corresponding receptacle 78 on the bottom enclosure 62 to connect the lid to the bottom enclosure. Additionally, the lid may be fixedly connected to the bottom enclosure to provide a tamper resistant seal. For example, the lid may be secured to the bottom enclosure by ultrasonic welding. In another example, adhesive may be applied to the locking tabs so as to bond the lid to corresponding receptacles on the bottom enclosure.

Figure 2:
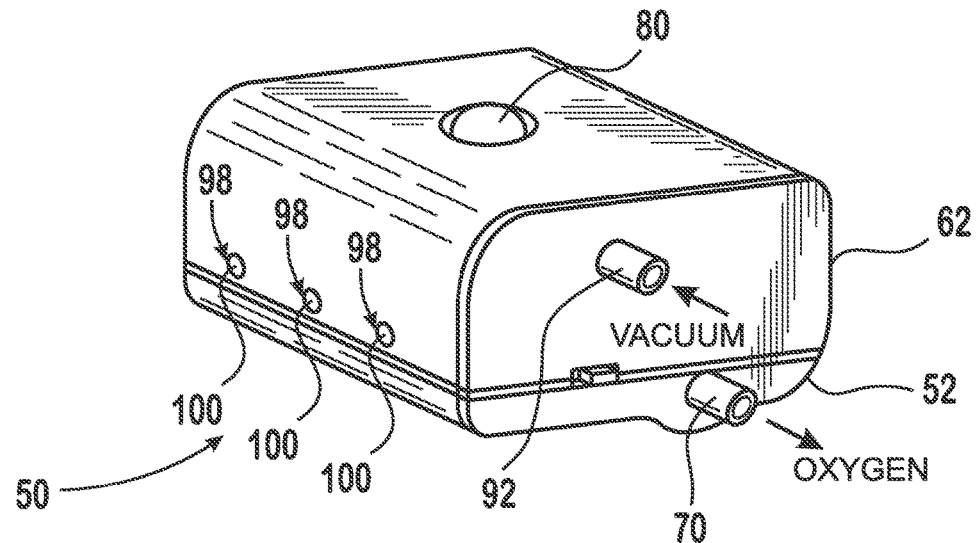
FIG. 2 is a perspective view of another embodiment of a wound care device in accordance with the present invention.
Figure 3:
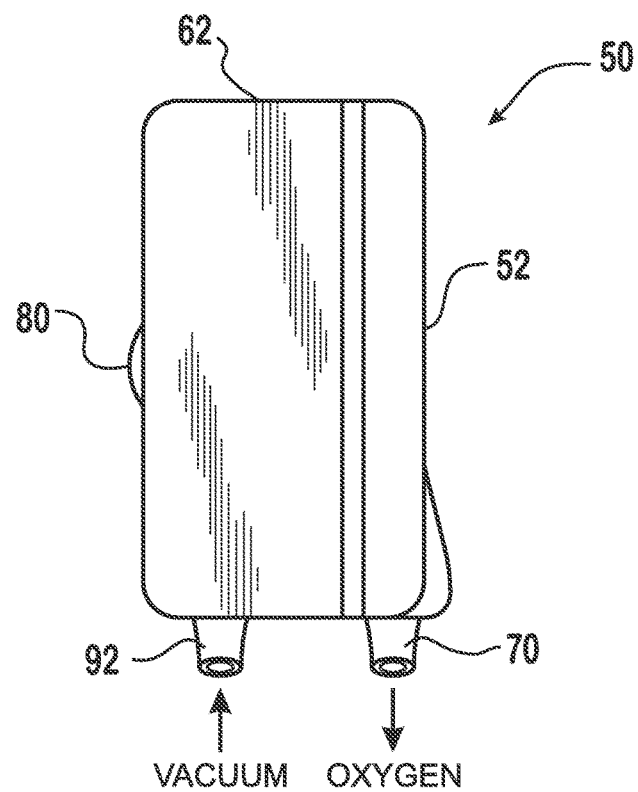
FIG. 3 is a side view of the wound care device of FIG. 2.

Referring to FIG. 2 and FIG. 3, the housing further may include a power switch 80. Although the power switch may be a button switch, any suitable switching device may be used as long as the switching device provides reliable operation and is resistant to inadvertent operation. In one embodiment, the switching device may require the application of significantly greater force to deactivate (or power off) the device than to activate (or power on) the device. In another embodiment, two hands may be required to manipulate one or more safety locks in order to deactivate the device. In another embodiment, a tool may be required to deactivate the device. The power switch may be centrally located on one side of the device, and the oxygen concentrating device 68 and oxygen port 70 may be located on an another side of the device.

As shown in FIG. 1, the bottom enclosure 62 may include a power and/or air supply chamber 82 for supplying air and electricity to the oxygen concentrating device. For example, the base of the power and air supply chamber may be shaped to receive and hold a power supply for the device. Additionally, the middle and upper portion of the power and air supply chamber may be configured to securely accommodate a PCB upon which the control circuit for the device may reside. In the exemplary embodiment, the PCB includes pairs of terminals 84 which clip to individual batteries 86 and thus mechanically secure and electrically connect the power supply to the PCB and/or control circuit.

The bottom enclosure further may include a mechanical pump chamber 88. The mechanical pump chamber 88 may be physically separated from the power and air supply chamber by a wall 90 so as to reduce the risk that operation of the mechanical pump may adversely impact oxygen concentration and delivery processes. The mechanical pump chamber 88 may be configured and dimensioned to securely receive the vacuum pump (e.g., an electrically powered mechanical pump) 60 which may be used to evacuate gaseous substances and exudates from the wound environment. The mechanical pump chamber may include an exterior wall. The exterior wall may include another tubular port 92. The other tubular port 92 may have a passageway 94 that extends from the tip of the tubular port to an interior surface of the mechanical pump chamber. Further, the bottom enclosure 62 may include openings (e.g., notches or pin holes) 96 in the exterior walls of the mechanical pump chamber in order to vent pump exhaust from the housing. Also, the bottom enclosure may include attachment sites (e.g., receptacles for locking tabs) 78 for connecting the lid to the bottom enclosure.

As shown in FIG. 2, the housing may include openings 98 for a number of status indicators 100. For example, individual LEDs may be positioned in each opening to signal operational modes or alarms.

Referring to FIG. 1, the oxygen concentrating device 54 may include a membrane electrode assembly (MEA) 102 for the electrochemical production of oxygen from air or water. For example, an ion conducting membrane 104 may be positioned between two electrodes 106 which in turn are connected to a power source. Oxygen in ambient air may be reduced to water at an interface region of the MEA between the cathode held at a reducing potential and the membrane. The product water may be moved through the membrane to the anode held at an anodic potential, which oxidizes the water back to oxygen while releasing protons at an interface region between the anode and the membrane. The protons may move through the membrane to the cathode to make possible continued reduction of oxygen from air. Atmospheric nitrogen and carbon dioxide, however, which are electrochemically inert under the reaction conditions required for oxygen reduction, are effectively rejected at the cathode. Accordingly, the reduction product of oxygen alone moves through the membrane, resulting in nearly 100% pure oxygen on the anode. An oxygen producing device for wound care is discussed in U.S. Pat. No. 7,429,252, which is incorporated herein by reference in its entirety.

The ion conducting membrane 104 may be any of a number of known ion conducting membranes which are capable of conducting protons and other ionic species. Suitable membranes may include various perfluoronated ionomer membranes which include a poly(tetrafluoroethylene) backbone and regularly spaced perfluoronated polyether side chains terminating in strongly hydrophilic acid groups. A preferred group of membranes suitable for use in the MEA include those containing sulfonic acid terminating groups on the side chains and available under the trademark Nafion® from E.I. Dupont Co. Nafion® is a perfluorinated polymer that contains small proportions of sulfonic or carboxylic ionic functional groups. Other suitable membranes may include partially fluorinated membrane materials and those based on hydrocarbon polymer backbones.

The electrodes 106 used in the membrane electrode assembly may be in the form of a mesh or a thin coating on the opposite surfaces of the membrane. In general, the electrodes may be made of any materials which are electrically conductive and which will catalyze the reduction of gaseous oxygen into water, provide a voltage differential across the membrane to move the oxygen containing species, and catalyze the oxidation of the product water to release oxygen. Suitable electrode materials include, but are not limited to, platinum, iridium, rhodium, and ruthenium, as well as their alloys and oxides in a pure finely divided form or as supported catalysts.

Referring to FIG. 1A, one method of making a membrane electrode assembly includes bonding a Pt/C electrode and a Pt black electrode 106 to either side of a Nafion® (or similar) membrane 104. The electrical connections from the electrodes 106 to the voltage source (or power supply) may be provided through conducting end plates which may be made of graphite or metallic material. To reduce weight and improve mobility of the device, a thin (e.g., 1-5 mil), electrically conducting and electrochemically inert wire is placed between the membrane and electrode during the bonding process, thereby making the electrical connection an integral part of the membrane electrode assembly. Examples of such wires include: gold, Pt, gold or Pt plated or deposited Ta, or tungsten, and other conducting materials such as carbon fiber.

In addition, a catalyst may be used to improve the electrochemical production of oxygen in the above reactions. The addition of a catalyst in one or both electrodes aids in overcoming kinetic reaction barriers. Preferably, a Pt—Ru, Pt—Ir, or similar noble metal alloy catalyst that is poison resistant is used to coat the electrodes. The use of such poison resistant catalysts will prevent impurities introduced from the adhesive and other components of the device from reducing the catalyst activity and deactivating the device. Suitable non-limiting examples of anode catalysts include Pt—Ir, Pt—Sn, and ternary combinations thereof. Suitable non-limiting examples of cathode catalysts include Pt—Ru/C, Pt—Sn, Pt—Ir, Pt—C, and ternary combinations thereof.

Each electrode further may be covered with a gas permeable/liquid impermeable barrier layer 110. The gas permeable/liquid impermeable barrier layer may be heat bonded to the electrode. These barrier layers may protect the polymer membrane, which otherwise might be damaged by contaminating foreign solids or liquids. Preferably, the gas permeable/liquid impermeable barrier layer may be formed from ePTFE (i.e., expanded polytetrafluoroethylene).

The MEA electrodes 106 may be connected to the control circuit via conductive wire(s) 108 embedded in each respective electrode.

Figure 1B:
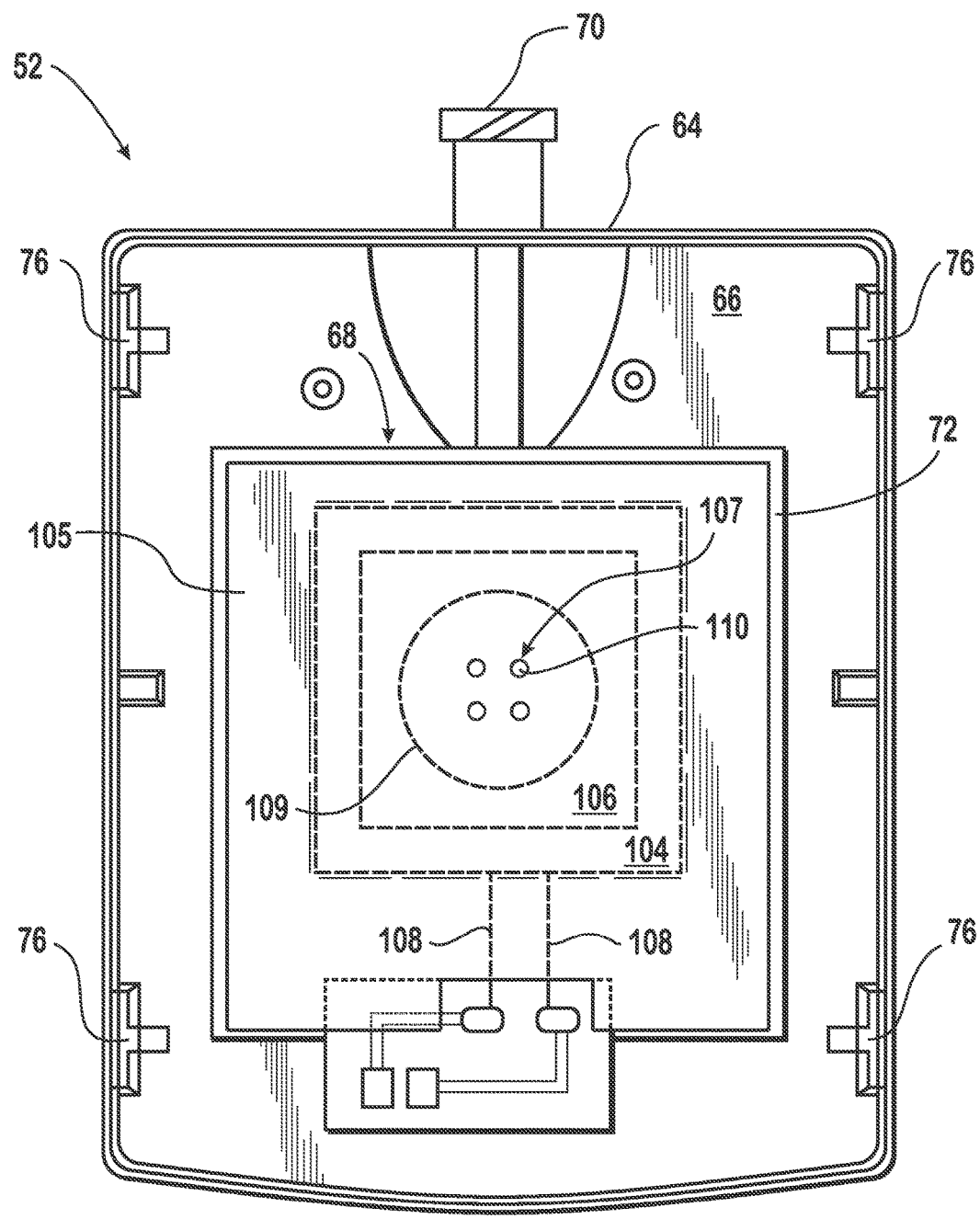
FIG. 1B is a plan view of the interior side of the lid of the wound care device of FIG. 1, including a cover for reducing moisture loss from the MEA.

FIG. 1B shows a plan view of an exemplary embodiment of a cover 105 for the MEA 102 of FIG. 1A. The cover 105 may protect the MEA 102 or regulate the conditions under which the MEA operates. The cover may be designed to limit evaporation of moisture from the MEA 102. The cover may be designed to enhance electrical insulation between the MEA 102 and other components (e.g., electronic devices on PCB 56) of the wound care device. The cover 105 may be formed from a substantially liquid and gas impermeable material.

The cover may include one or more holes (or passages) 107 which provide a pathway for air to pass through the cover. Generally, one hole having a radius of approximately 0.159 mm may provide minimally sufficient airflow through the cover based on a diffusion transport model calculation. The cover may be positioned over the MEA such that the holes (or passages) 107 are disposed over the cathode electrode air opening 109 in the adhesive layer 72. The remaining components of the MEA 102 may remain as described in connection with the lid sub-assembly of FIG. 1A. The cover further may possess electrical or thermal insulating properties.

Preferably, the cover may be formed from a polyimide film and silicone adhesive (e.g., DuPont™ Kapton® tape). Although the cover may be formed from Kapton, other suitable materials may be used (e.g., Teflon (PTFE), polyethylene, and Mylar (biaxially-oriented polyethylene terephthalate)) provided that the cover limits moisture evaporation from the MEA while allowing adequate air access to the electrode, and (2) substantially prevents electrical contact of the electrode with electronic components of the PCB 56 (see e.g., FIG. 1) by providing an insulating surface.

The cover also may be formed from one or more layer(s) (and/or sections) of material(s), which may include one or more holes so long as the cover limits moisture evaporation from the MEA while allowing adequate air access to the electrode. Preferably, the cover also substantially prevents electrical contact of the electrode with electronic components of the PCB 56 (see e.g., FIG. 1) by providing an insulating surface.

In the embodiment of FIG. 1B, four small holes 107 may be punched (or formed) in the Kapton cover. The holes 107 may be generally uniform in size. For example, each of the four holes may form a passage through the cover. Each hole may have a cross-sectional area of approximately 0.01 cm$^2$.

The holes 107 may be generally uniform in shape. For example, the holes may be substantially circular.

Alternatively, the cover may include holes which vary in size or shape. In the embodiment of FIG. 1D, the holes 107 in the cover include a set of passages having cross-sectional areas with three different shapes and sizes. The holes 107 may be elongated having similar width and differing length, and may be arranged in parallel.

Figure 1C:
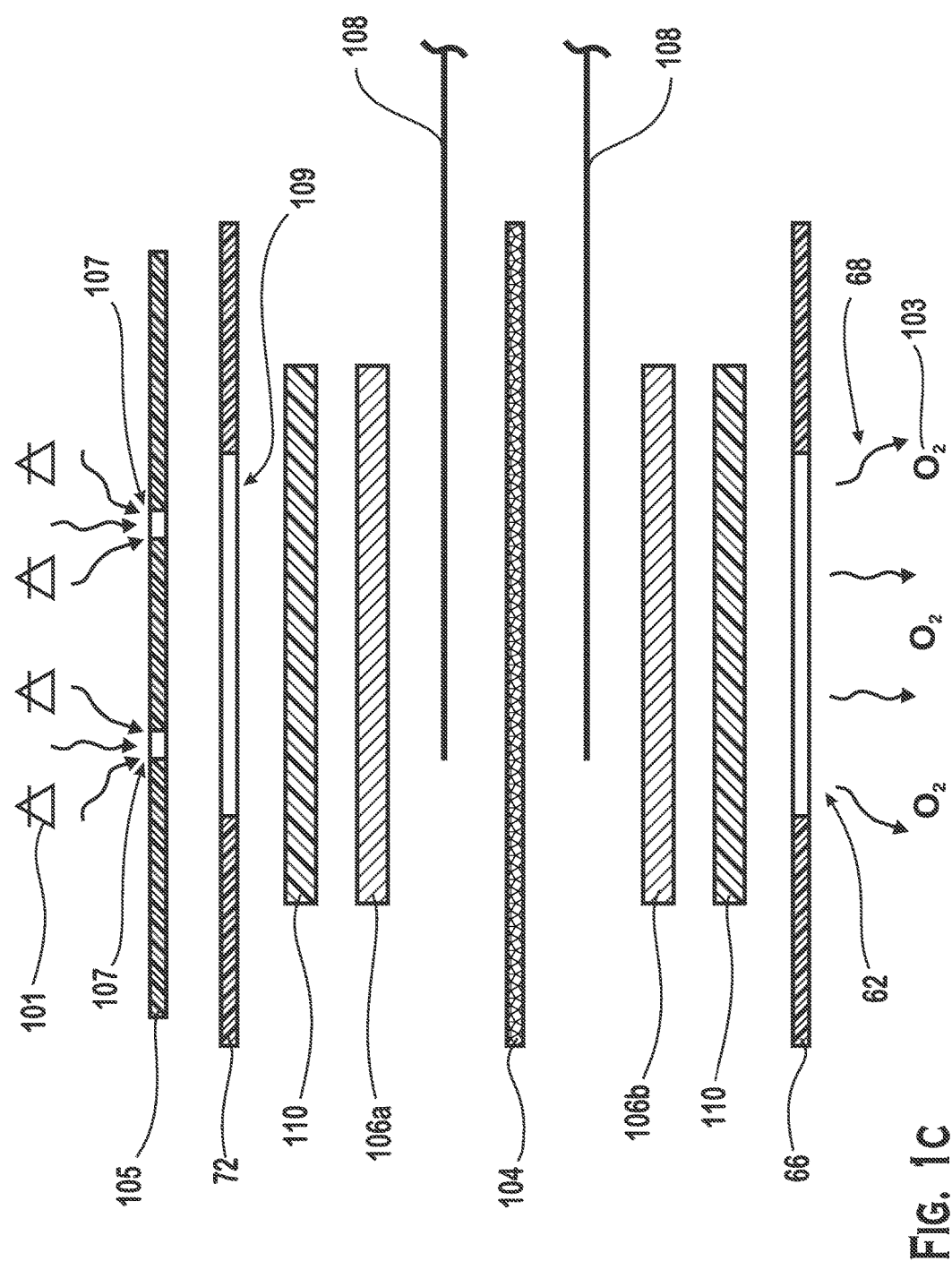
FIG. 1C is an exploded schematic view of the interior side of the lid of the wound care device of FIG. 1B.
Figure 1D:
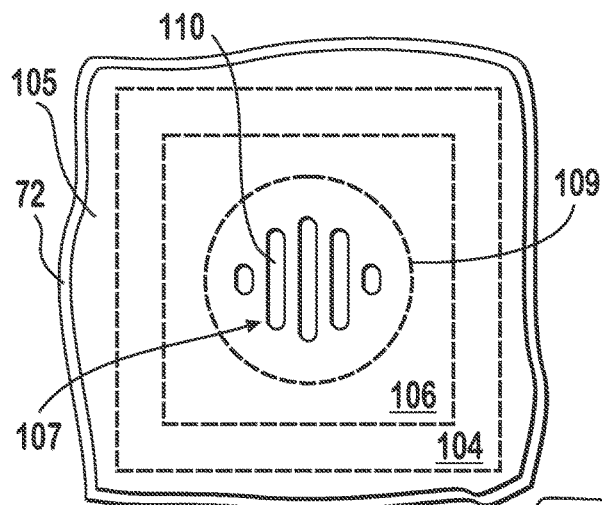
FIG. 1D is a partial plan view of another embodiment of a cover for the MEA of FIG. 1B.
Figure 1E:
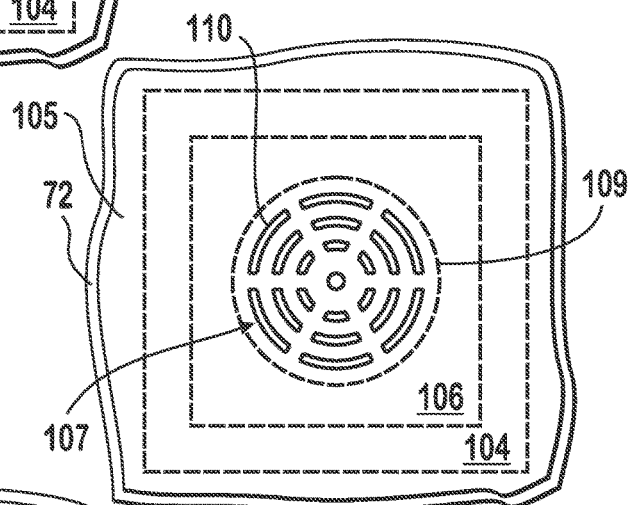
FIG. 1E is a partial plan view of another embodiment of a cover for the MEA of FIG. 1B.

In the embodiment of FIG. 1E, the holes 107 in the cover include a generally centrally located passage having a cross-sectional area of circular shape, and six sets of curved passages of differing length that are disposed in a generally concentric pattern about the centrally located passage.

Figure 1F:
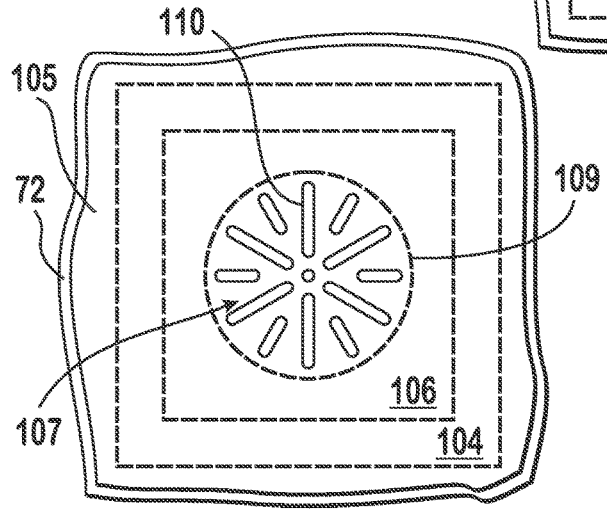
FIG. 1F is a is a partial plan view of another embodiment of a cover for the MEA of FIG. 1B.

In the embodiment of FIG. 1F, the holes 107 in the cover include a generally centrally located passage having a cross-sectional area of circular shape, and two sets of elongated segments of differing length that are disposed in a generally radial alignment about the centrally located passage.

Referring to FIG. 1C, during operation of the MEA 102 air 101 may pass through the holes (or passages) 107 in the cover 105, as well as the gas permeable/liquid impermeable barrier layer covering the cathode electrode 106a. Oxygen in the air 101 may be reduced to water at an interface region of the MEA between the cathode 106a held at a reducing potential and the membrane 104. The product water may be moved through the membrane 104 to the anode 106b held at an anodic potential, which oxidizes the water back to oxygen 103 while releasing protons at an interface region between the anode 106b and the membrane 104. The protons may move through the membrane to the cathode 106a to make possible continued reduction of oxygen from air. Atmospheric nitrogen and carbon dioxide, however, which are electrochemically inert under the reaction conditions required for oxygen reduction, are effectively rejected at the cathode. The reduction product of oxygen alone moves through the membrane, resulting in nearly 100% pure oxygen 103 on the anode 106b. The oxygen 103 may then collect in the oxygen collection chamber 68 of the mounting surface 66 of the lid, which may then be transported out of the device for clinical use. In one embodiment, the mounting surface may include a silicon adhesive tape. For example, the mounting surface 66 may include a double coated tape or film that includes adhesive on both sides of the tape or film. One side of the double coated tape or film may adhere to the lid 52 (see FIG. 1B) and the other side of the double coated tape or film may face and adhesively receive other components of the MEA.

Accordingly, the cover 105 may reduce the area of the cathode electrode 106b that is exposed to air 101. The cover 105 may improve performance in two areas. First, reducing the area of the cathode air opening 109 may help reduce moisture loss from the MEA 102. This may improve MEA voltage stability under dry ambient conditions (e.g., ambient relative humidity substantially equal to or less than 30%). Second, the cover 105 may electrically insulate the cathode electrode from nearby circuit board components. This may prevent stray currents from being generated between the cathode electrode and the circuit board components.

In the embodiment of FIG. 1A, electrical contact between the cathode electrode and the circuit board components potentially may occur should a patient sit on the device during use. The weight of the patient on the device may depress the MEA lid subassembly sufficiently to bring the cathode into contact with the circuit board components. Insulating properties of the cover of FIG. 1B may provide sufficient electrical insulation between the MEA and these components to prevent the generation of stray currents between the cathode electrode and the circuit board components.

Six MEAs were fabricated in accordance with the disclosure of commonly owned U.S. Pat. No. 7,429,252. The six MEAs were used to make lid sub-assemblies in accordance with the embodiment of FIG. 1A. The MEA electrodes of each lid sub-assembly were generally square and measured approximately 0.75 inches on a side. The six lid sub-assemblies were placed on a test stand, and the MEAs of each lid sub-assembly were tested. More particularly, the MEA electrodes of each lid sub-assembly were electrically connected to a current source that delivered a total current of 13.5 mA, and the voltage across the cathode electrode and the anode electrode of the MEA (MEA Voltage) was measured using a multimeter manufactured by BK Precision. The initial values of MEA Voltage for each lid sub-assembly are presented in Table 1.

After initial testing, a Kapton cover was applied to each of three lid sub-assemblies as shown in FIG. 1B. All six lid sub-assemblies were tested again to measure the MEA voltage, and testing continued for 15 days. The results (Notebook 130-73) are shown in Table 1.

TABLE 1

MEA Voltage of Exemplary Lid Sub-Assemblies

| | | | MEA Voltage, V | | | |
|---|---|---|---|---|---|---|
| No. | Description of Test Article | Initial MEA Voltage, V | Day 0 14 RH % | Day 2 14 RH % | Day 7 18 RH % | Day 16 10 RH % |
| 1 | No Kapton cover | 1.059 | 1.089 | 1.133 | 1.159 | 3.219 |
| 2 | No Kapton cover | 1.057 | 1.082 | 1.137 | 1.187 | 3.126 |
| 3 | No Kapton cover | 1.022 | 1.051 | 1.102 | 1.102 | 1.704 |
| 4 | Kapton cover applied | 1.173 | 1.206 | 1.269 | 1.269 | 1.358 |
| 5 | Kapton cover applied | 1.204 | 1.209 | 1.287 | 1.331 | 1.484 |
| 6 | Kapton cover applied | 1.113 | 1.162 | 1.223 | 1.278 | 1.348 |

Notes:
(a) MEA Voltage was recorded for a total current of 13.5 mA.
(b) RH %, ambient relative humidity as measured by Lascar Humidity Meter at approximately 68° F.

Table 2 shows the change in MEA Voltage from Day 0 to Day 16. The MEA Voltage in the three lid sub-assemblies increased by more than 60%. By contrast, the MEA Voltage in the three lid sub-assemblies with the Kapton cover increased by less than 25%.

TABLE 2

MEA Voltage Stability of Exemplary Lid Sub-Assemblies

| | | MEA Voltage, V | | | |
|---|---|---|---|---|---|
| No. | Description of Test Article | Day 0 | Day 16 | Difference | % Increase |
| 1 | No Kapton cover | 1.089 | 3.219 | 2.130 | 196% |
| 2 | No Kapton cover | 1.082 | 3.126 | 2.044 | 189% |
| 3 | No Kapton cover | 1.051 | 1.704 | 0.653 | 62% |
| 4 | Kapton cover applied | 1.206 | 1.358 | 0.152 | 13% |
| 5 | Kapton cover applied | 1.209 | 1.484 | 0.275 | 23% |
| 6 | Kapton cover applied | 1.162 | 1.348 | 0.186 | 16% |

Additionally, testing was conducted to validate performance of the lid sub-assembly of FIG. 1B. Fifty lid sub-assemblies were constructed for validation testing with an EPIFLO® oxygen concentrator. In the first part of the validation testing, the test devices were switched on and monitored for oxygen generation and LED function over a normal 15-day operating period. The tested devices successfully completed the 15-day operating test.

In the second part of the validation testing, ten lid sub-assemblies of the original 50 lid sub-assemblies constructed for the validation testing were mechanically tested by placing a 30-pound weight on the lid. The weight was concentrated directly on the center of the lid where the MEA electrodes are located. The test was intended to simulate conditions that might be experienced if a user were to inadvertently sit on the device during use. The MEA lid subassemblies were installed on the test stand, and the MEA voltage was measured with and without the weight in place. The results are presented in Table 3.

TABLE 3

Effect of 30 lb. Weight on MEA Voltage for Test Devices with Kapton Cover.

| | Device # | | | | | | | | | |
|---|---|---|---|---|---|---|---|---|---|---|
| | 1 | 2 | 3 | 4 | 5 | 6 | 7 | 8 | 9 | 10 |
| $V_1$ (no weight) | 0.876 | 0.920 | 0.940 | 0.875 | 0.967 | 0.936 | 0.940 | 0.925 | 1.009 | 0.916 |
| $V_2$ (30 lb. weight) | 0.880 | 0.914 | 0.916 | 0.878 | 0.968 | 0.938 | 0.945 | 0.931 | 1.004 | 0.917 |

Note:
MEA Voltage measured in Volts.

The validation testing results showed that the weight did not affect the MEA voltage. After the weight was removed, the ten lid sub-assemblies were examined to evaluate whether contact between the MEA and circuit board components had penetrated the Kapton cover. The results showed that there was no damage to the MEA from the circuit board components.

The amount of oxygen generated by the MEA 102 may be varied by changing the current applied to the electrodes. Typically, the device may produce between approximately 1 ml oxygen/hr and approximately 50 ml oxygen/hr, more preferably between approximately 3 ml/hr and approximately 10 ml/hr.

The mechanical pump 60 may be disposed in the mechanical pump chamber 88. The mechanical pump may be a miniature diaphragm pump and may be driven by a DC motor. At standard conditions, the pump may operate over a pressure range of approximately 0 kPa to 165 kPa and a vacuum range of approximately 0 mmHg to 500 mmHg. The maximum unrestricted flow of the pump may be approximately 2.5 liters per minute (LPM). Operation of the mechanical pump may be controlled via pulse width modulation of the DC motor. One commercially available pump which may be suitable for this application is a 2.5 LPM CTS Micro Diaphragm Pump manufactured by Parker Hannifin Corporation.

The pump intake may be connected to a manifold that includes a pressure sensor, a check valve, and a liquid isolation filter (e.g., a micron filter disc). The manifold, in turn, may be connected to the vacuum port 92, which may be connected via external tubing to a waste canister and wound dressing. The pump discharge may be connected to a filter-muffler to assist with filtration and provide noise reduction. The pump discharge may be released into the mechanical pump chamber 88. As described above, the mechanical pump chamber further may include a number of notches or perforations 96 for releasing pump discharge exhaust to the housing exterior.

The PCB 56 may include control circuitry for operating the oxygen concentrating device, the mechanical pump, and the LED status indicators. The control circuit also may include circuitry or devices for managing power from the power supply. The control circuit may include a microprocessor and memory, a microcontroller, or an ASIC, along with other semiconductor devices and electronic components to provide the desired functionality Although the control circuit may include a microprocessor or programmable microcontroller to provide the device with enhanced functionality (e.g., user selection and adjustment of therapy settings), the control circuit may be implemented with basic controls and capabilities in order to provide a simple yet robust device that is suitable for use in acute care or home care settings. Preferably, the functionality of the device will include therapy monitoring based on measurements of MEA current usage as well as the pressure range of the mechanical pump vacuum intake.

For example, the device control system may monitor the oxygen delivery rate and signal one or more status indicators should the MEA system cease to operate according to the prescribed therapy. Also, the device may monitor the pressure of the mechanical pump vacuum intake in order to determine whether there is a leak (i.e, the intake vacuum is less than the therapeutic range) or a blockage (i.e., the intake vacuum is greater than the therapeutic range) in the dressing or vacuum application line. Also, the device control system may signal one or more status indicators that the device and dressing apparatus are operating in accordance with the prescribed therapy.

The power supply 58 may include one or more electrical batteries 86. Preferably, the power supply may have a high energy density so as to provide maximum power for minimum volume and weight. Non-limiting examples of battery types that may be suitable for the power supply include lithium-ion, alkaline and metal hydride batteries. Each battery may be manufactured according to a predetermined life span. For example, without limitation, the batteries may be designed to supply power continuously to the wound care device for at least 5, 7, or 10 days.

Different sized batteries may be incorporated into a single oxygen producing device. Other types of power sources include batteries, fuel cells, photovoltaic cells and supercapacitors in combination with one or more of the above power sources. Although the control circuit, MEA, mechanical pump, and status indicators may be powered by one power supply, independent power supplies may be provided for one or more of these components. Also, as previously described, the PCB may clip securely to the power supply.

Referring to FIG. 1 and FIG. 2, the oxygen port 70 and the vacuum port 92 may conform to a standardized system of small-scale fluid fittings that are used for making leak-free connections between a male-taper fitting and its mating female part. For instance, the oxygen port and the vacuum port may each include a Luer Lock fitting.

Figure 4:
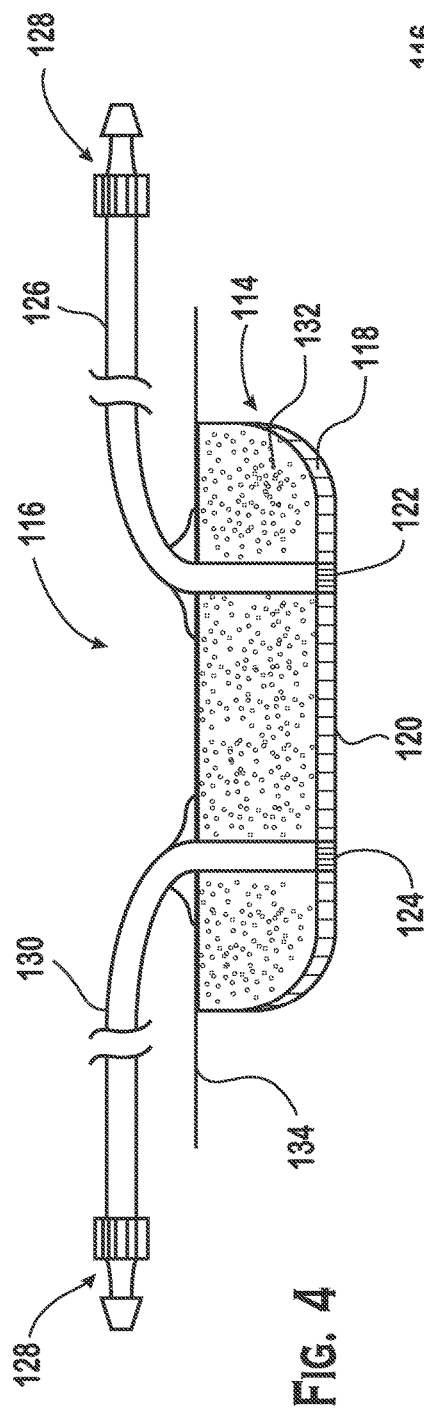
FIG. 4 is a cross-sectional view of an embodiment of a dressing assembly in accordance with the present invention.
Figure 5:
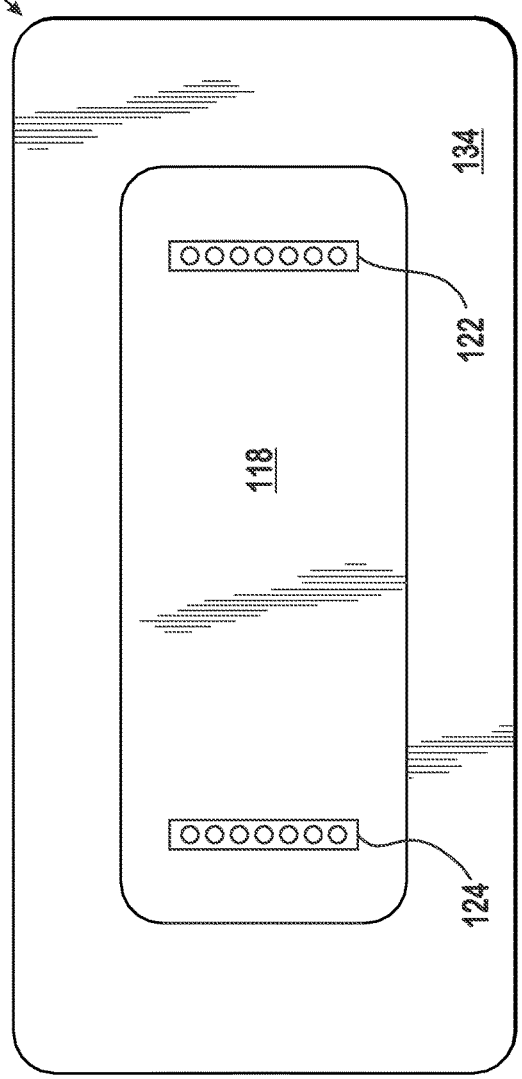
FIG. 5 is a schematic plan view of the dressing assembly of FIG. 4.

FIG. 4 shows an illustrative wound bed 114 prepared for NPWT and transdermal continuous oxygen therapy (TCOT) with an exemplary embodiment of a dressing 116 in accordance with the present invention. The TCOT/NPWT dressing 116 may include a wicking layer which abuts and covers the wound bed 120. The wicking layer 118 may be made from moisture-wicking synthetic fabric (e.g., Under Armour® or similar fabric). The wicking layer 118 may draw exudates away from the wound and aid in establishing contiguous flow of oxygen across the wound bed 120. The wicking layer may include an oxygen delivery manifold 122 to encourage topical delivery of oxygen to the wound. Additionally, the wicking layer may include a mixed gas and exudates removal manifold 124. This manifold may facilitate distributed oxygen flow across the wound bed, and may promote waste gas and exudates removal from the wound. As shown in FIG. 5, the manifolds 122, 124 may be placed contra-laterally above the wound bed 120 to promote oxygen flow distribution and enhance contact time. The oxygen delivery manifold 122 may be connected to a first length of flexible tubing 126. The first length of flexible tubing 126 may include a standardized fluid fitting (e.g., Luer Lock fitting) 128 for connecting the other end of the flexible tubing to the oxygen port 70 of the wound care device 50. Similarly, the waste gas and exudates removal manifold 124 may be connected to a second length of flexible tubing 130. The second length of flexible tubing 130 may include a standardized fluid fitting (e.g., Luer Lock fitting) 128 for connecting the other end of the second length of flexible tubing to an intermediate waste canister or directly to the vacuum port 92 of the wound care device. The tubing may be made from a polymeric material suitable for use in hospital applications. Suitable materials for use in the tubing include, but are not limited to, silicone, polyethylene, polypropylene, polyurethane and various other thermoplastics.

The dressing 116 further may include an absorbent layer 132 above the manifold and wicking layer 118. The absorbent layer 132 may hold exudates that are transported through the wicking layer. The absorbent layer 132 may provide structural support for the wound, the manifold and the first and second lengths of tubing. Additionally, the absorbent layer 132 may provide a protective barrier for the wound bed against physical trauma or microorganisms. In one embodiment, the absorbent layer may be gauze. In another embodiment, the absorbent layer may be polyurethane foam.

The dressing 116 further may include a semi-occlusive layer 134. The semi-occlusive layer may be a sheet of transparent film. The sheet of transparent film may include adhesive on one side to help create an air tight seal around the perimeter of the wound bed. The semi-occlusive layer 134 may include penetrations for passage of the first and second lengths of tubing. The penetrations may be located above the dressing manifolds. Sealant may be applied around the penetration and the flexible tubing to form air tight seals. In one embodiment, the sheet of film may be a Tegaderm® dressing manufactured by 3M.

Figure 6:
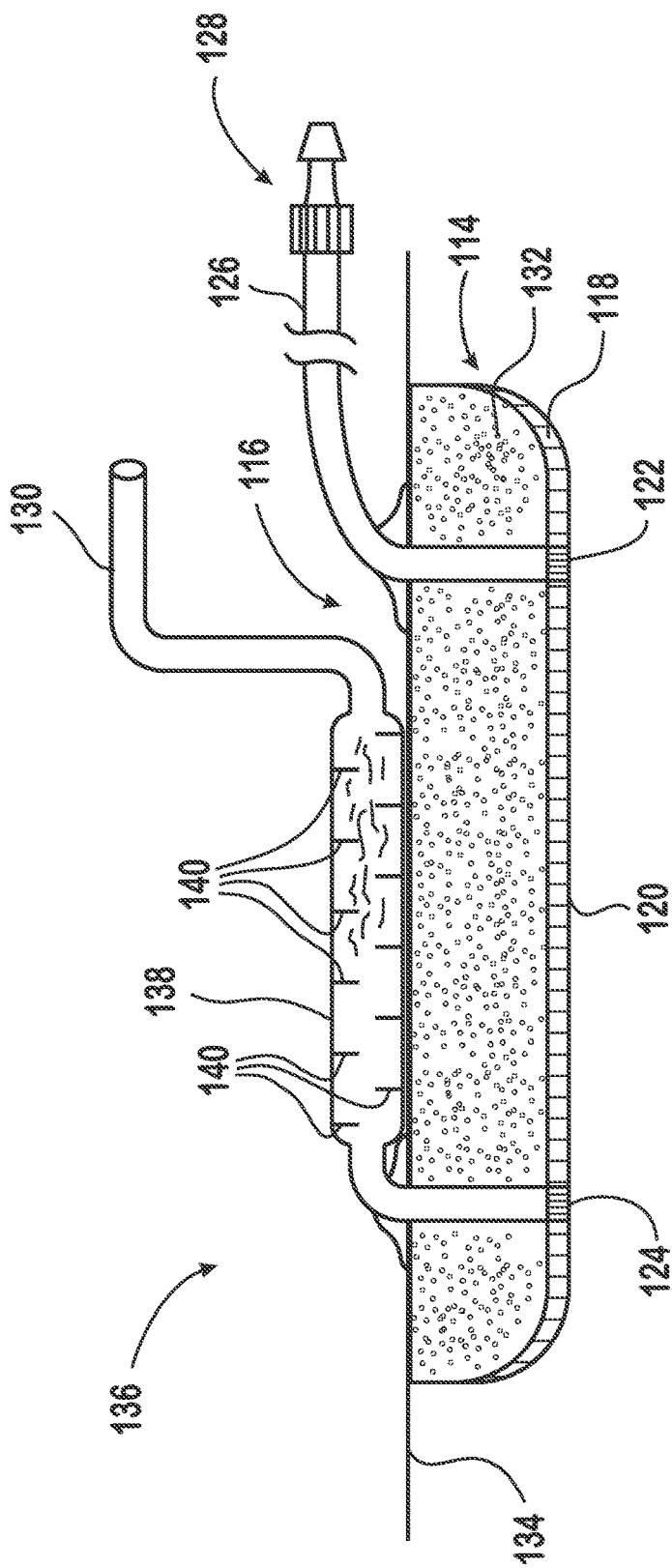
FIG. 6 is a cross-sectional view of another exemplary dressing assembly with a storage accessory for exudate in accordance with the present invention.

FIG. 6 shows an illustrative wound bed prepared for NPWT and TCOT therapy with another exemplary embodiment of a dressing 136 in accordance with the present invention. This embodiment is similar to the dressing of FIG. 4 as described above. This embodiment, however, includes an integral bag 138 for storing waste exudates. The integral bag 138 may be flexible and possess a low profile to facilitate patient comfort and mobility. The integral bag 138 may include internal spacers 140 which may prevent flexible portions of the bag from collapsing and occluding exudates and waste gas flow under negative pressure.

Figure 7:
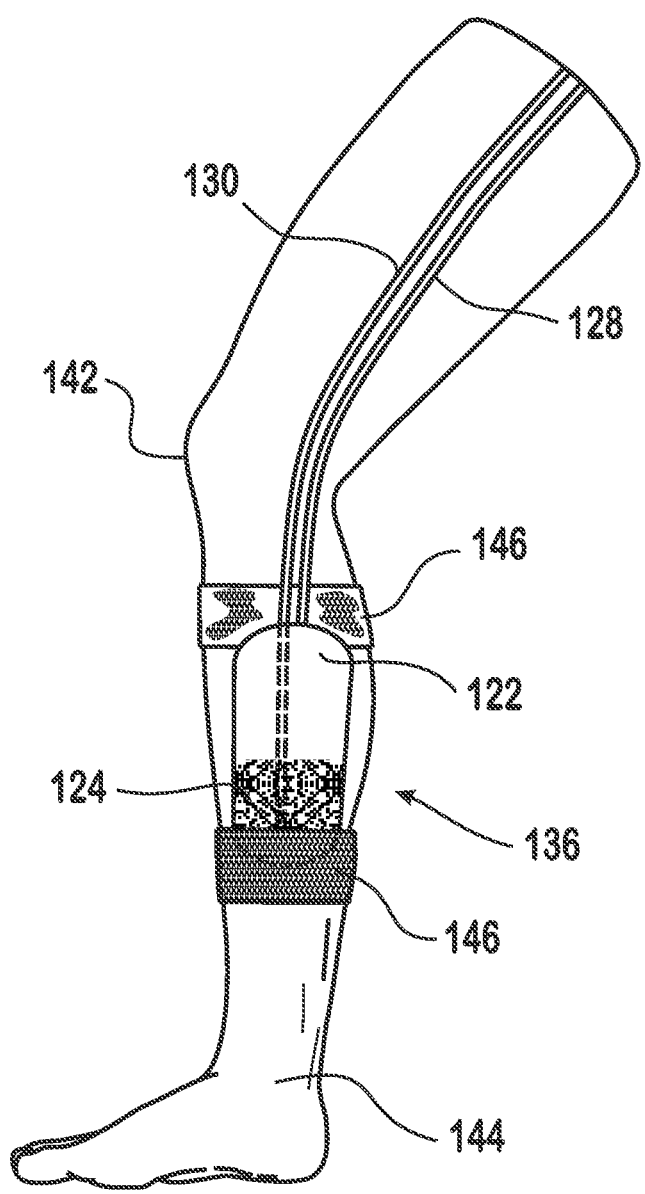
FIG. 7 is a schematic view of the dressing of FIG. 4 mounted on a leg wound of a human patient.

FIG. 7 shows a schematic representation of the dressing of FIG. 6 applied to a leg wound of a patient. The dressing 136 may be oriented such that the oxygen delivery manifold 122 is closer to the patient's knee 142 and the mixed gas and exudates removal manifold (or vacuum application manifold) 124 is closer to the patient's ankle 144. The dressing 136 and flexible tubing 128, 130 may be secured with a strap 146 at the top end and the bottom end of the dressing assembly to allow the patient to ambulate. Additional straps may be used to secure the vacuum supply tubing and the oxygen delivery tubing along the length of the patient's leg. The straps may have fastening elements for providing an adjustable fit. The fastening elements may be hook and loop fasteners (e.g., Velcro® strips).

Figure 8:
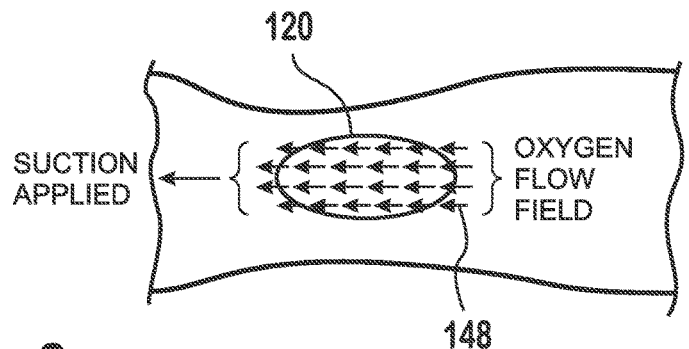
FIG. 8 is a schematic view of transdermal oxygen flow through the dressing and across the wound of FIG. 5.

FIG. 8 shows a schematic representation of mass flow 148 across an exemplary wound 120 being treated with NPWT and transdermal oxygen therapy. During one mode of therapy, oxygen at a maximum rate of approximately 3 cc/hr to approximately 4 cc/hr may be continuously directed to the wound bed by the oxygen delivery manifold. Concurrently, the vacuum application manifold may apply negative pressure to the wound bed to create a maximum return-gas flow rate of approximately 1 cc/hr. It is believed that the balance of oxygen delivered to the wound bed may be naturally absorbed or consumed by tissue in or around the wound. During application of this therapy, the head space of the wound inside the dressing assembly may stabilize at an oxygen concentration in the range of approximately 20 percent to 75 percent. Preferably, however, the head space of the wound inside the dressing assembly may stabilize at an oxygen concentration of approximately 70 percent. The non-oxygen head space gases in the dressing may include tissue off gases (e.g., carbon dioxide) from natural processes such as respiration from the wound.

Oxygen delivery pressure may adjust to whatever pressure may be needed to accommodate the generation rate of oxygen determined by the current flow. Oxygen delivery pressure to the dressing may be slightly greater than the pressure in the headspace of the wound environment in order for the oxygen to flow to the wound. For example, the oxygen delivery pressure may reach an average pressure of approximately 680 mmHg absolute because the pressure in the headspace of the wound environment may range from approximately 660 mmHg to 680 mmHg. The vacuum level at the wound may be adjusted by the control system to achieve the desired therapeutic conditions. In this operable configuration, the MEA may operate under a constant current mode to enable oxygen generation. For example, the MEA may generate oxygen at a rate of 3 cc/hr. Although the controller may vary the level of the current in order to adjust the rate of oxygen production, the MEA may be operated at a constant current so the flow of oxygen to the wound may be maintained by the backpressure of oxygen in the MEA assembly, the vacuum applied to the wound space by the mechanical pump, and respiration of the wound. The control system may vary the vacuum level by activating the mechanical pump. The mechanical pump speed further may be controlled through pulse width modulation.

Periodically, in another mode of therapy, the mechanical pump speed may be set to zero and the polarity of the MEA reversed. Under these conditions, the MEA may operate under constant voltage to generate a vacuum at the oxygen delivery manifold. The vacuum generated by the MEA may range from approximately 1 mmHg to approximately 50 mmHg. The reduction in negative pressure applied by the MEA in this mode of therapy may benefit healing processes in the wound by temporarily reducing wound tissue strain. A wound healing device for the application of oxygen and the removal of wound exudates is discussed in U.S. Pat. No. 8,088,113, which is incorporated herein by reference in its entirety.

Figure 9:
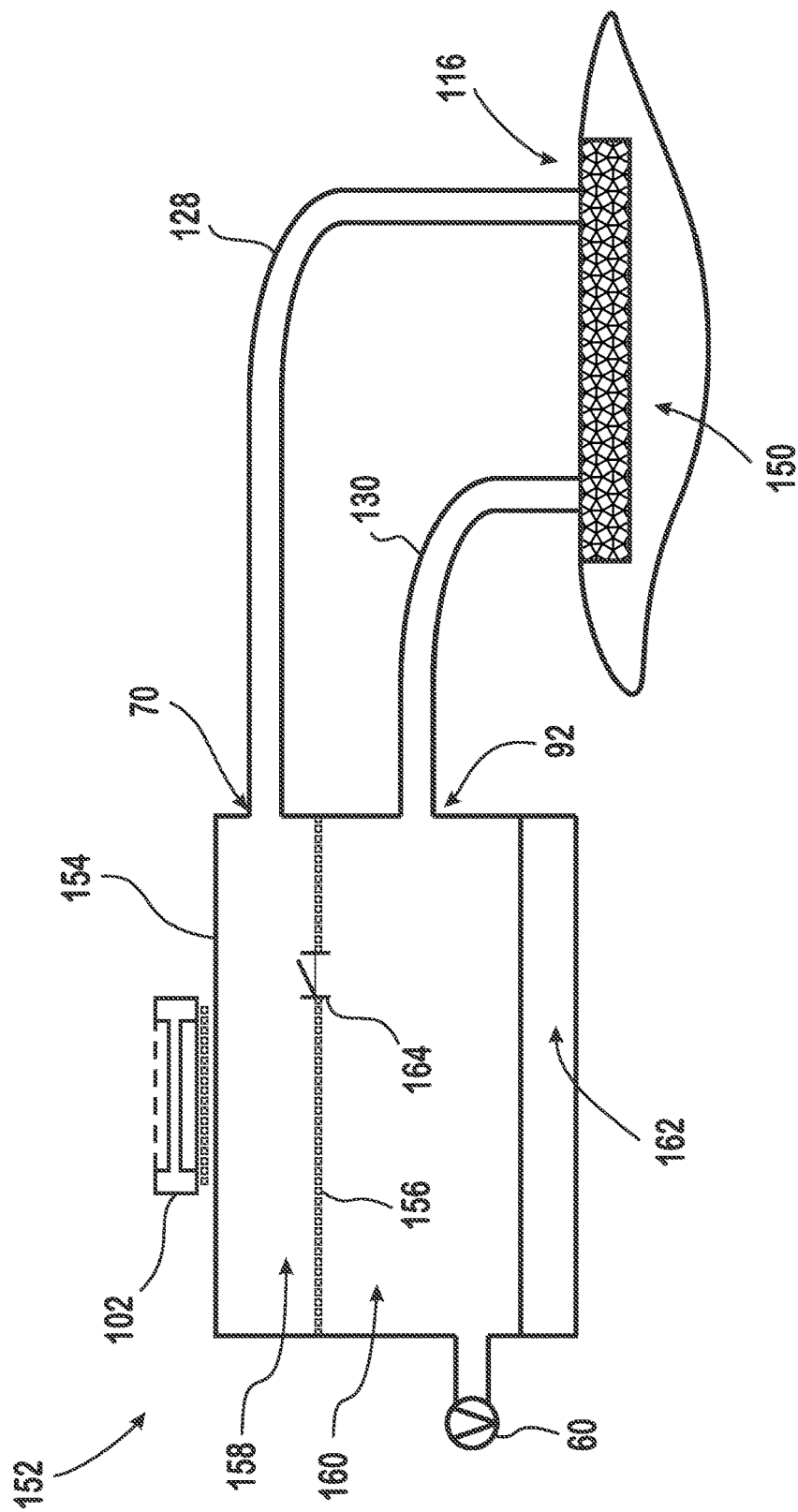
FIG. 9 is a schematic view of another exemplary device for delivering NPWT and transdermal oxygen flow through a dressing and across a wound in accordance with the present invention.

FIG. 9 shows a schematic diagram of another embodiment of a wound care device 152 connected to a dressing 116 for applying transdermal oxygen therapy and negative pressure wound therapy to a wound 150. The apparatus may include an MEA 102, a vacuum pump 60, and a housing 154 for these components. The housing may include a gas/liquid barrier 156 between the MEA 102 and the mechanical pump 60. The gas/liquid barrier 156 may divide the housing 154 into two chambers. The first chamber 158 of the device may include the MEA (or cell) and oxygen port. The MEA may interact with air outside the housing to produce nearly pure oxygen in the first chamber. The second chamber 160 of the device may include the intake of the vacuum pump and the vacuum port 92. The mechanical pump intake may include a fitting that includes a pressure sensor and a liquid impermeable filter. The second chamber may include a liquid trap 162 for storing or containing exudates that have been evacuated from the wound 150 and drawn into the housing 154 under negative pressure. A check valve 164 connecting the two chambers 158, 160 may allow gas flow from the second chamber 160 to the first chamber 158. The check valve 164 may be a flap valve. The oxygen port 70 may be connected via flexible tubing 128 to a dressing 116 for delivering oxygen to the wound 150. The vacuum port 92 may be connected via flexible tubing 130 to the dressing to apply negative pressure to the wound 150. The liquid trap 162 may operate based on mechanical principles or chemical-mechanical principles. The liquid trap 162 may be designed to operate independently of the device's orientation. In another embodiment, the treatment device of FIG. 9 may be designed with the exudates trap on the outside of the housing. An external exudates trap may be removable from the housing.

Figure 10:
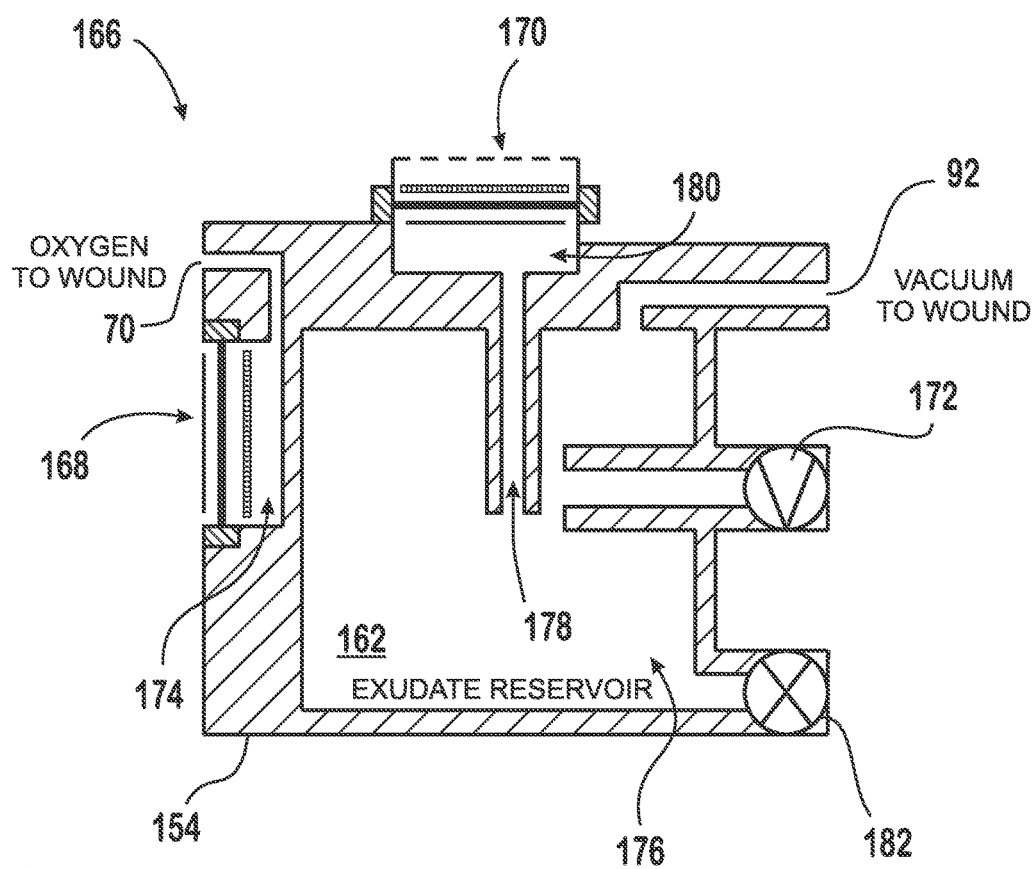
FIG. 10 is a schematic view of yet another exemplary device for delivering NPWT and transdermal oxygen flow through a dressing and across a wound in accordance with the present invention.

FIG. 10 shows a schematic diagram of another device 166 that may be used with a dressing 116 to simultaneously apply transdermal oxygen therapy and negative pressure wound therapy to a wound. The device may include two MEAs 168, 170, a mechanical pump 172, and a housing 154. The device 166 may include a first MEA 168 that concentrates oxygen in a first internal compartment 174 of the housing. The first internal compartment 174 may be connected to an oxygen port 70 for delivery to the wound. The vacuum pump intake 92 may be connected a second internal compartment 176 in the housing. The second internal compartment 176 may be connected to a vacuum port 92 for applying negative pressure to the wound. The second MEA 170 may be configured to consume oxygen from the exudates reservoir 162 and contribute to, or when operating alone create, a negative pressure in the second internal compartment 176. A passage 178 may connect the second internal compartment 176 to the third internal compartment 180 adjacent the second MEA 170. In this embodiment, one MEA 168 may be dedicated to generating oxygen for the oxygen port 70 and another MEA 170 may be dedicated to generating negative pressure in the second compartment 176 and vacuum port 92. The second internal compartment 176 further may include a drain 182 for removing exudate evacuated from the wound via negative pressure. The second internal compartment 176 may be configured to store exudates independent of the housing orientation. The device may be connected to a dressing via flexible tubing.

FIG. 11 shows another embodiment of a wound care device 184 in accordance with the present invention. The wound care device 184 may include an exterior housing 186. The housing may include two or more sections. The sections may be connected to form an enclosure for holding and containing internal components of the wound care device. In this embodiment, the housing may include two sections 186a, 186b which may be secured together to form a tamper resistant, water resistant enclosure.

The enclosure may house process equipment, electronic controls, communication devices, and power supply equipment that enable a mobile and self-contained wound care device which is capable of providing a portable oxygen supply and a portable vacuum supply for administering transdermal oxygen therapy, NPWT, light wound suction, and other prescribed wound care therapies involving combinations thereof.

The housing (or enclosure) 186 may include an oxygen supply port 70, a vacuum supply port 92, a vacuum pump exhaust port 188, and a power switch 190. One or more of the ports may include a Luer lock fitting. Also, the enclosure includes three status indicator windows 192a, 192b, 192c. One status indicator window 192a may include a light pipe for an LED that signals a low battery condition (i.e., a battery low indicator). A second status indicator window 192b may include another light pipe for another LED that signals whether there is a leak or blockage in the dressing or vacuum application line (i.e., pressure excursion indicator). The third status indicator window 192c may include yet another light pipe for yet another LED that signals whether the device is on and/or operating in accordance with the prescribed wound care therapy.

The enclosure 186 may be designed to possess a low profile configuration that prevents entanglement with other bodies or external objects. Thus, the enclosure may have a length (L) and a width (W) of approximately equal dimension, and a height (H) that is less than the other two dimensions. For example, the housing may have a length of approximately 2.75 inches, a width of approximately 2.625 inches, and a height of approximately 1.43 inches. The external features of the housing may be smooth and rounded.

As shown in FIG. 12, the wound care device may be connected to a retaining clip (or holster) 194 which may be secured to a belt or strap 196 for mounting on (or near) a patient. For example, the housing and retaining clip may form a press-fit connection. With respect to mounting the wound care device 184 within the retaining clip 196, the enclosure 186 may be considered to have a front side 198, a rear side 200, a right side 202, a left side 204, a top side 206, and a bottom side 208. The rear side 200 of the enclosure may face the retaining ring clip 194. The front side 198 of the enclosure may face away from the retaining clip. The top side 206 of the enclosure may include the power switch, and the bottom side 208 of the enclosure may include the oxygen supply port 70 and the vacuum supply port 92. The left side 204 of the enclosure may include the vacuum pump exhaust 188.

The enclosure 186 may be formed from plastic, a reinforced polymer material, metal alloy or other strong durable material suitable for use in a medical device. For example, the enclosure may be formed from ABS (acrylonitrile butadiene-styrene) plastic.

Figure 13:
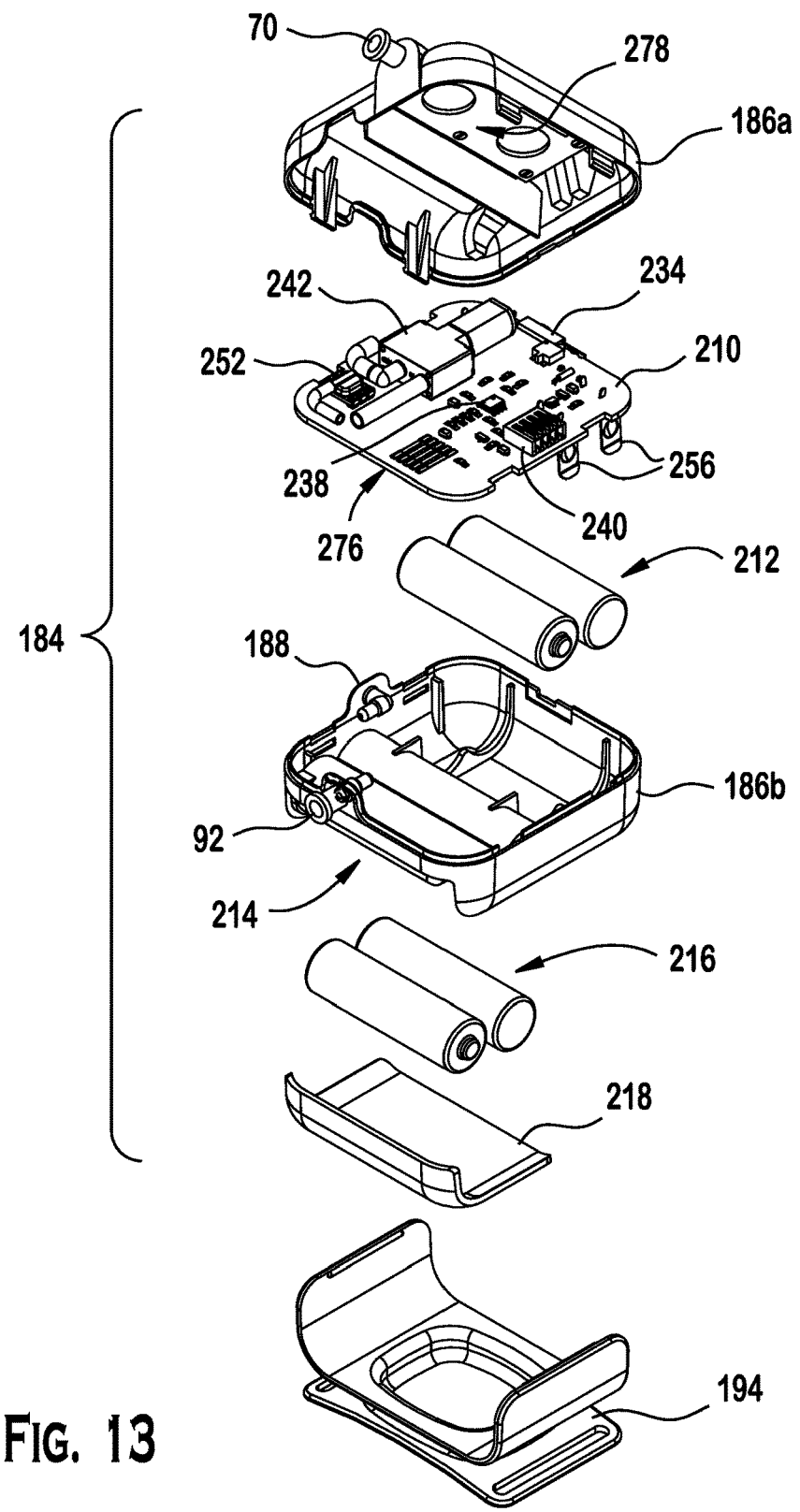
FIG. 13 shows an exploded view of the wound care device of FIG. 11.

Referring to FIG. 13, the wound care device may include a front enclosure section 186a, a printed circuit board 210, a fixed power supply 212, a rear enclosure section 186b that includes a replaceable power supply compartment 214, a replaceable power supply 216 and a cover 218 for the replaceable power supply compartment. The wound care device 184 further may include a retaining clip 194.

Figure 14:
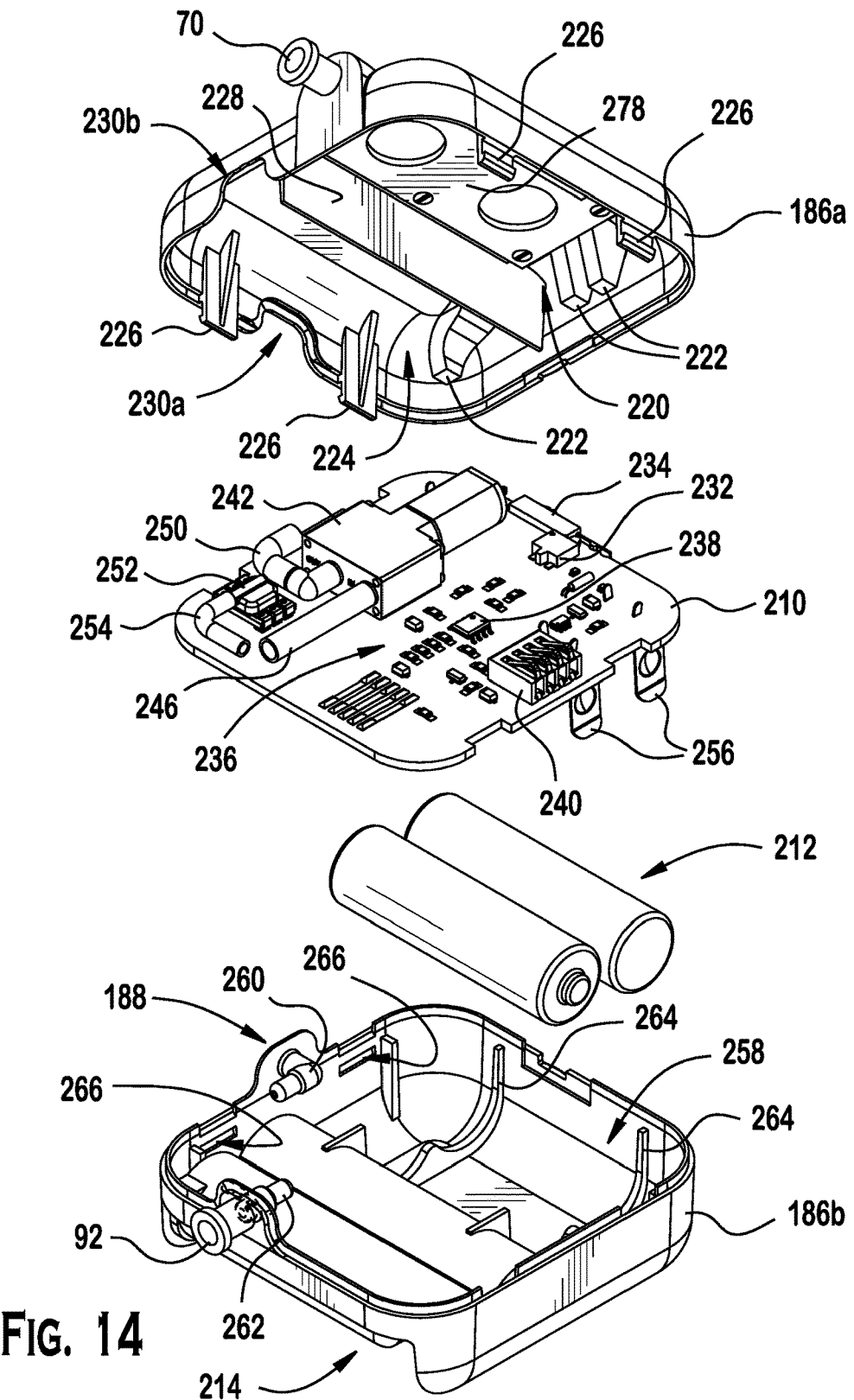
FIG. 14 shows a perspective view of components of FIG. 13.

As shown in FIG. 14, the front enclosure section 186a may include an oxygen supply port 70, an MEA assembly chamber 220, three light pipes 222, a vacuum pump chamber 224, and four locking tabs 226 for securing the front enclosure section to the rear enclosure section. A wall 228 may separate the MEA assembly chamber 220 from the vacuum pump assembly chamber 224. The front enclosure section further may include a cutout 230a in the left side wall and another cutout 230b in the bottom side wall.

Figure 15:
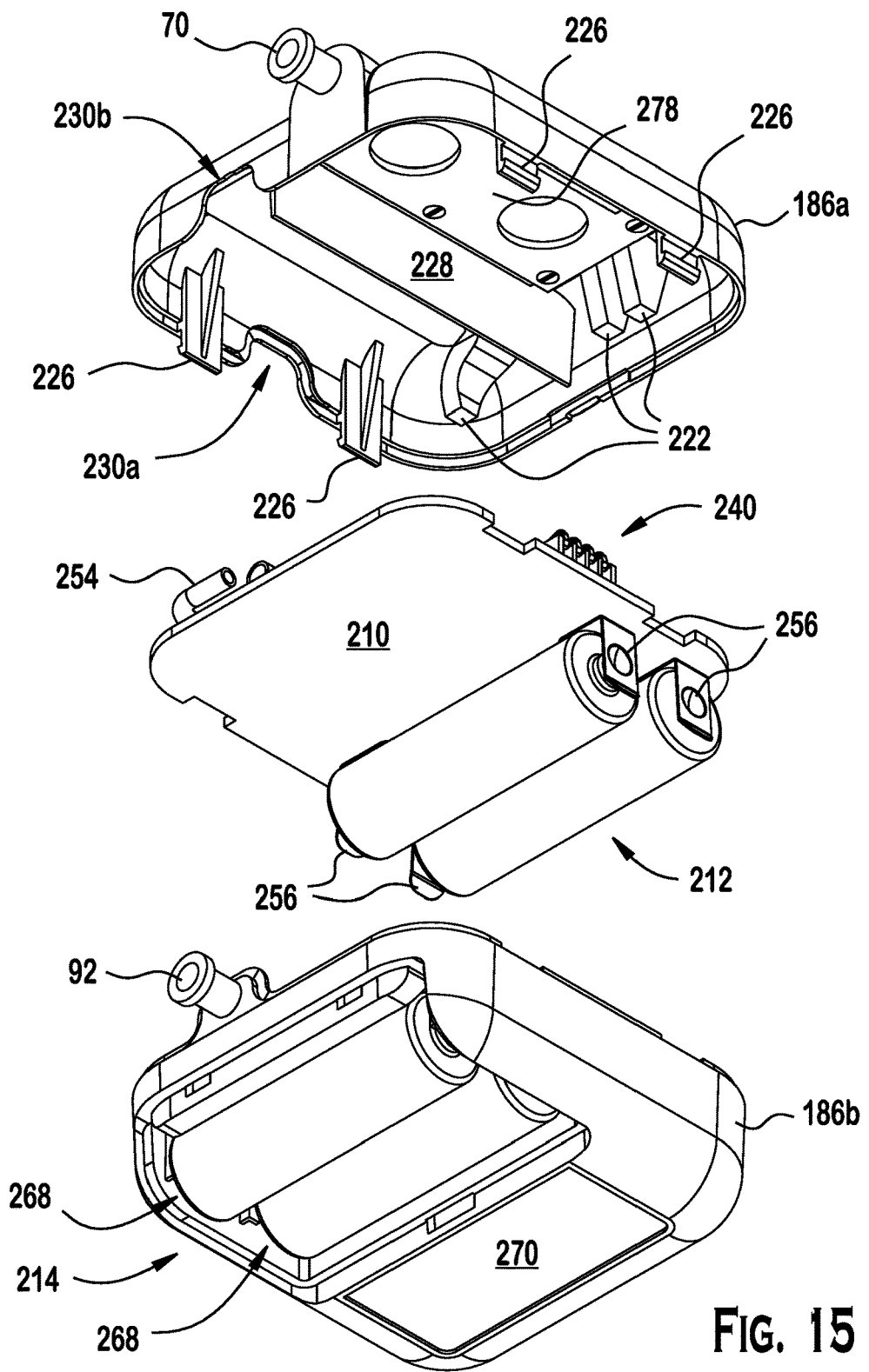
FIG. 15 shows another perspective view of components of FIG. 13.
Figure 16:
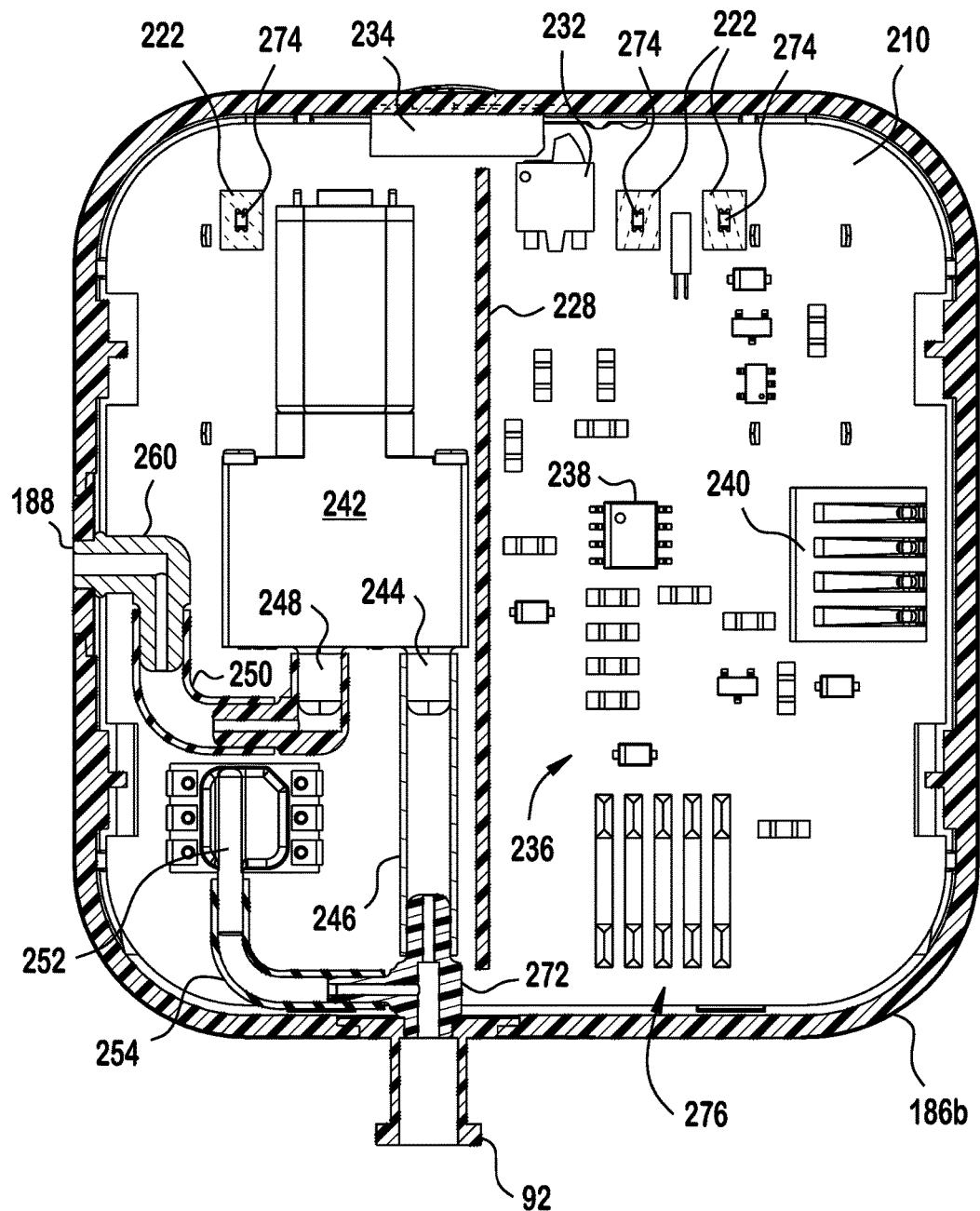
FIG. 16 is a plan view of an illustrative printed circuit board (PCB) and rear enclosure section of the device of FIG. 14.

Referring to FIG. 16, the PCB 210 may include a power switch 232 and a mechanical slide 234 for activating the power switch, process control circuitry 236 including a microcontroller 238, a contact spring assembly 240 for electrically connecting the control circuitry to the MEA assembly, a vacuum pump and motor assembly 242, a vacuum pump intake 244 and associated tubing 246, a vacuum pump discharge 248 and associated fittings and tubing 250, a pressure sensor assembly 252 and associated tubing 254, and dedicated MEA power supply terminals 256 (see FIG. 15). As shown in FIG. 15, the MEA power supply terminals 256 may be configured and dimensioned for a standard or custom battery type. The PCB 210 further may include a dedicated power supply circuit and a power supply (i.e., coin battery) for regulating operation of the wound care device.

Referring to FIG. 14, the rear enclosure section 186b may include an MEA power supply storage compartment 258, a vacuum pump exhaust port 188 and connector fitting 260, a vacuum supply port 92 and connector fitting 262, as well as power supply cradles 264, and receptacles for receiving the front enclosure section locking tabs 266. As shown in FIG. 15, the rear enclosure section 186b further may include a storage compartment 214 (and cover), as well as terminals 268 for a dedicated vacuum pump power supply. The vacuum pump power supply terminals 268 may be configured and dimensioned for a standard or custom battery type. The rear enclosure section 186b further may include a smooth, flat recessed surface 270 for receiving one or more product labels.

FIG. 16 shows a plan view of the PCB 210 mounted in the rear enclosure section 186b. The vacuum pump 242 is in fluid communication with the vacuum supply port 92. The vacuum pump intake port 244 is connected via tubing 246 to one branch of a T-fitting 272 that is connected to the vacuum supply port 92. The other branch of the T-fitting 272 is connected to a pressure sensor assembly 252 by a conduit 254. The conduit 254 may be flexible tubing. The vacuum pump discharge port 248 is in fluid communication with the vacuum pump exhaust port 188. The vacuum pump discharge port 248 is connected to a fitting that via tubing 250 is connected to another fitting that is connected to the vacuum pump exhaust port 188. Also, status indicator LEDs 274 may be positioned on the PCB. Each LED 274 may interact with a dedicated light pipe 222 to visually signal the status of selected operational processes. The PCB 210 further may include, without limitation, a set of contacts 276 for programming the microcontroller, as well as one or more power circuits. Additionally, the PCB 210 may include memory, a data bus, and/or wireless communication capabilities.

Figure 19:
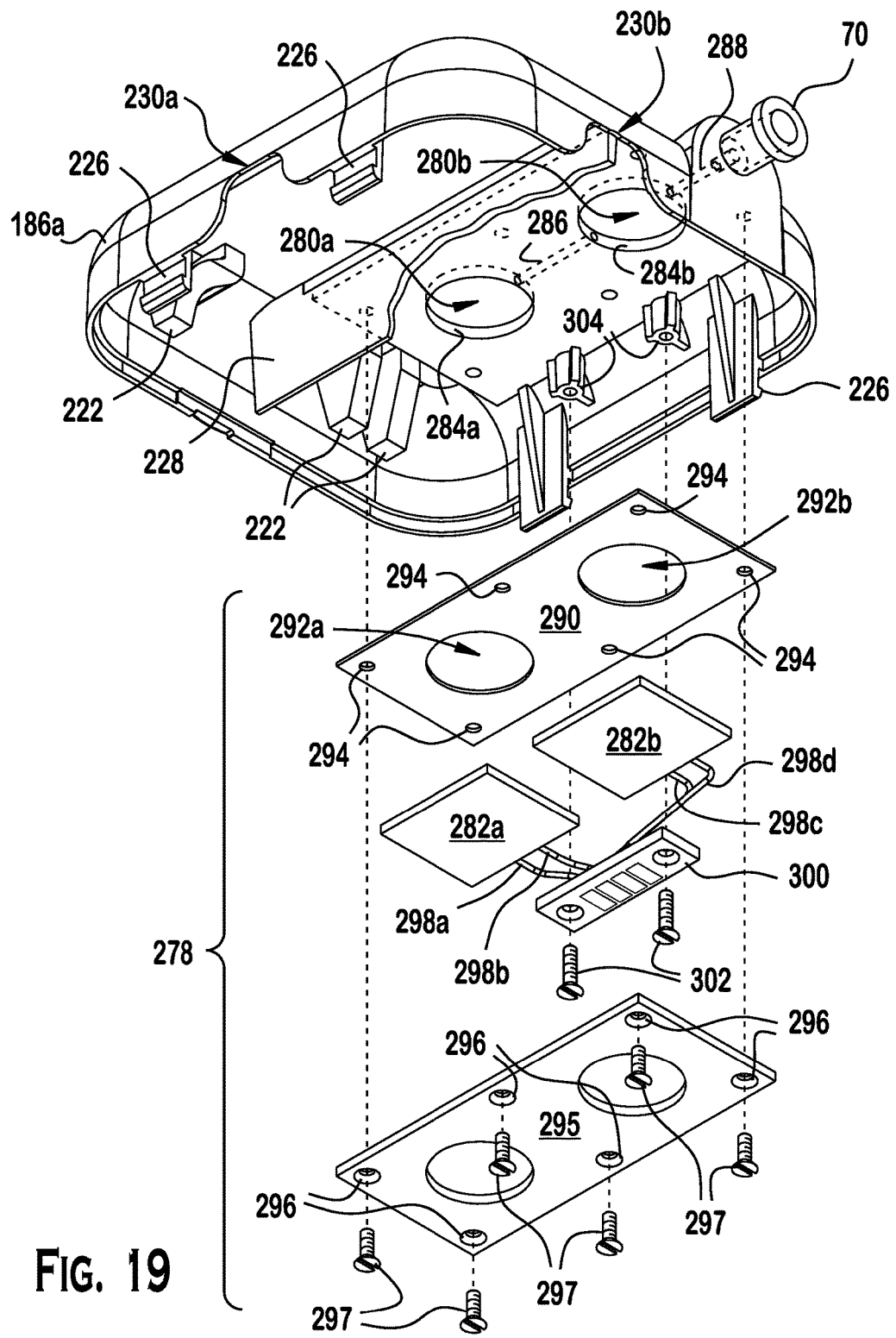
FIG. 19 is a perspective view of the front enclosure section of FIG. 18 and an exploded view of the MEA assembly.

Referring to FIG. 19, the MEA assembly 278 may be attached to the interior surface of the front enclosure section 186a. The interior surface of the front enclosure section may include two basins (or sink/recesses) 280a, 280b. Each basin 280a, 280b may be positioned under one MEA 282a, 282b. Each basin may further include a sidewall 284a, 284b. One sidewall 284a may be connected to the other sidewall 284b by an intermediate passage 286. Further, the other sidewall 284b may be connected to the oxygen supply port 70 by a distribution passage 288. Preferably, the intermediate passage 286 and the distribution passage 288 are aligned to facilitate fluid communication between the sinks 280a, 280b and the oxygen supply port 70.

Figure 17:
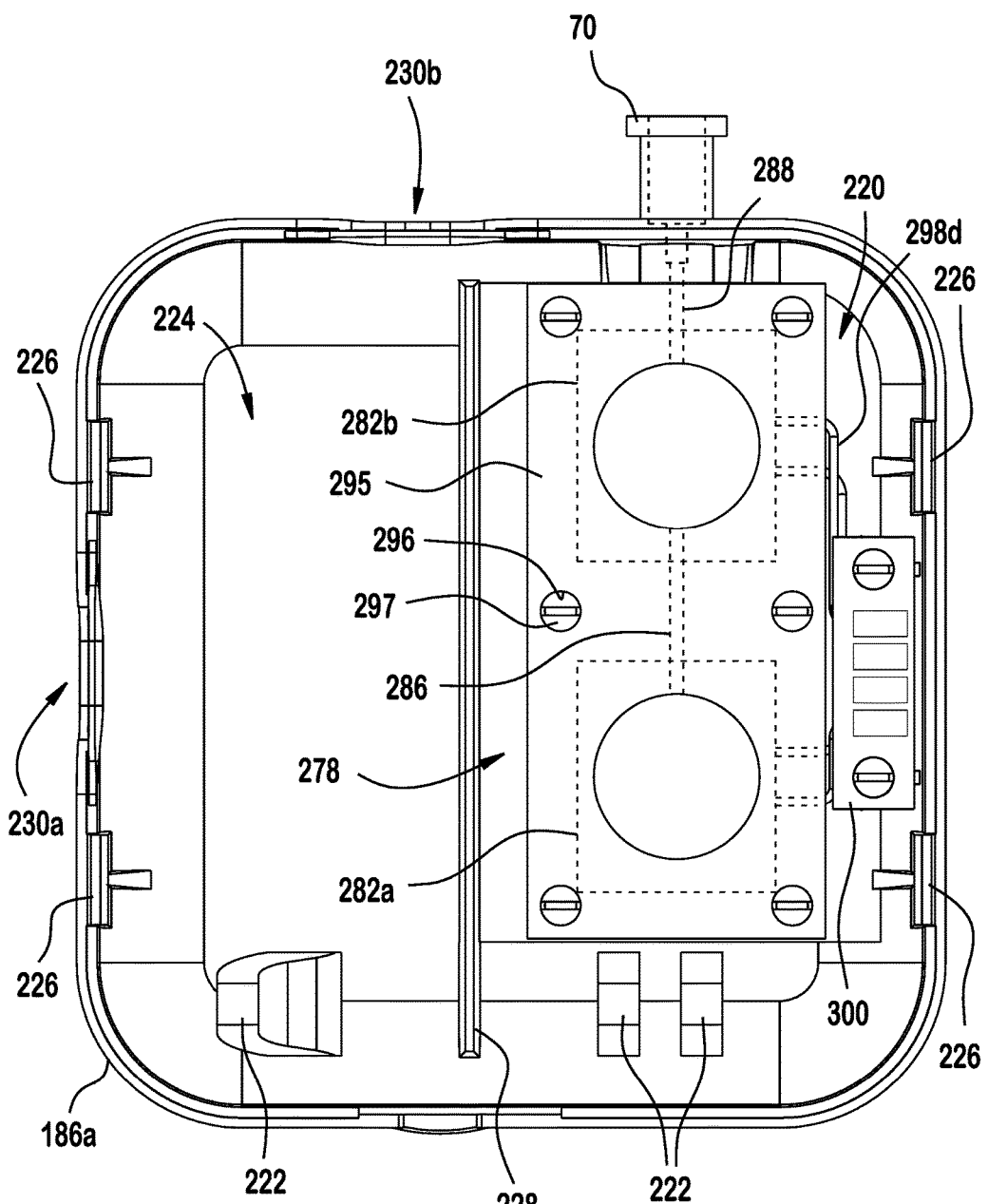
FIG. 17 is a plan view of the MEA assembly and front enclosure section of the wound care device of FIG. 14.
Figure 18:
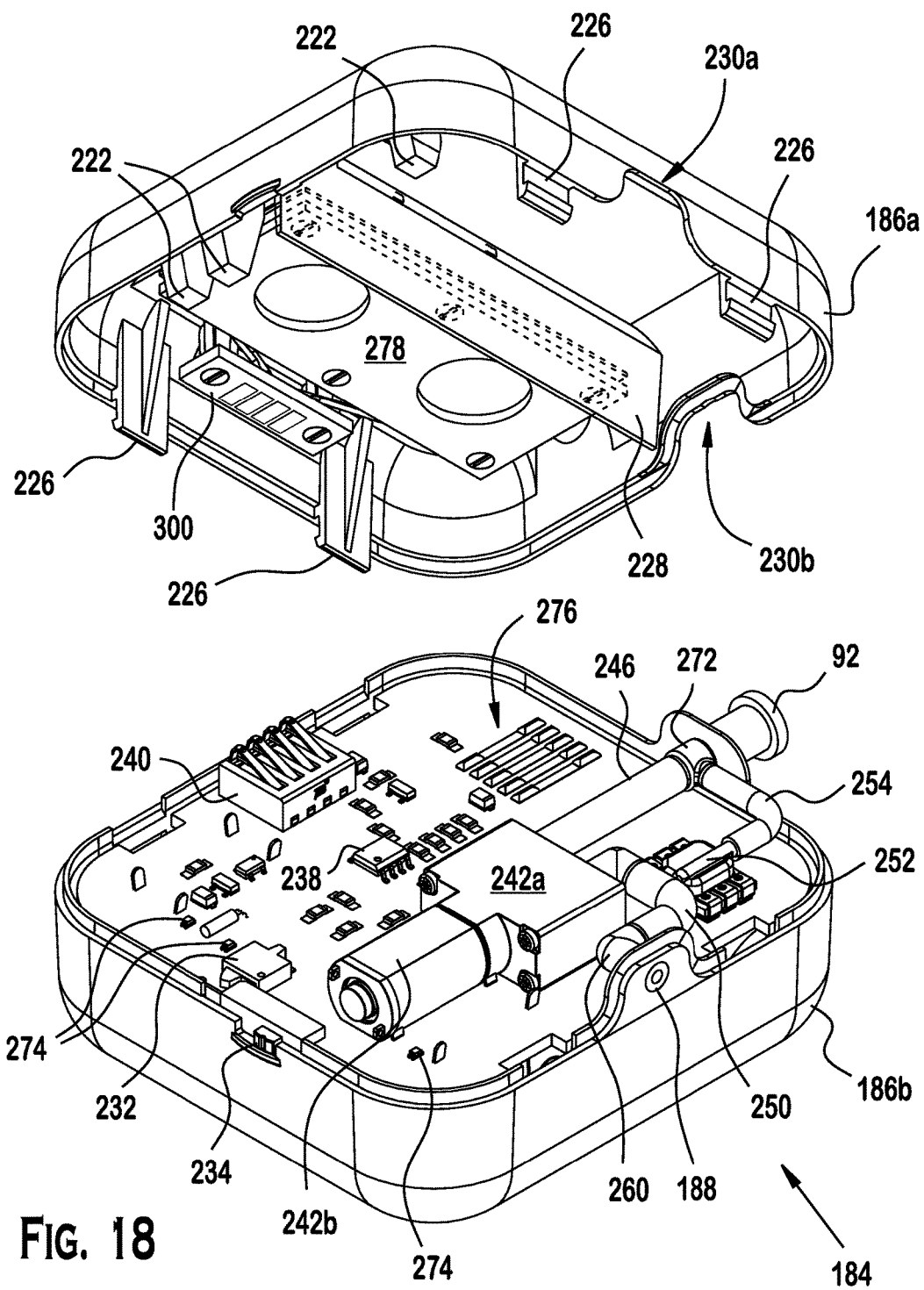
FIG. 18 is a perspective view of the wound care device of FIG. 11 with the front enclosure section removed.

The MEA assembly 278 may include an inert gasket 290 disposed between the MEAs 282a, 282b and the front enclosure section 186a. The gasket 290 may have holes 292a, 292b that conform to the shape and location of the sinks 280a, 280b, as well other holes 294 that are compatible with the MEA assembly. The MEAs 282a, 282b then may be clamped to the front enclosure section with a frame (or plate) 295. The frame 295 also may conform to the shape and location of the sinks 280a, 280b and may include holes 296 that present a pattern that conforms to the other holes 294. Further, the MEA electrodes may be connected via conductive wires 298a, 298b, 298c, 298d to a PCB landing pad 300. As shown in FIGS. 17 and 18, the PCB landing pad 300 may be secured with screws 302 to a dedicated seat 304 located adjacent to the MEAs.

Figure 20:
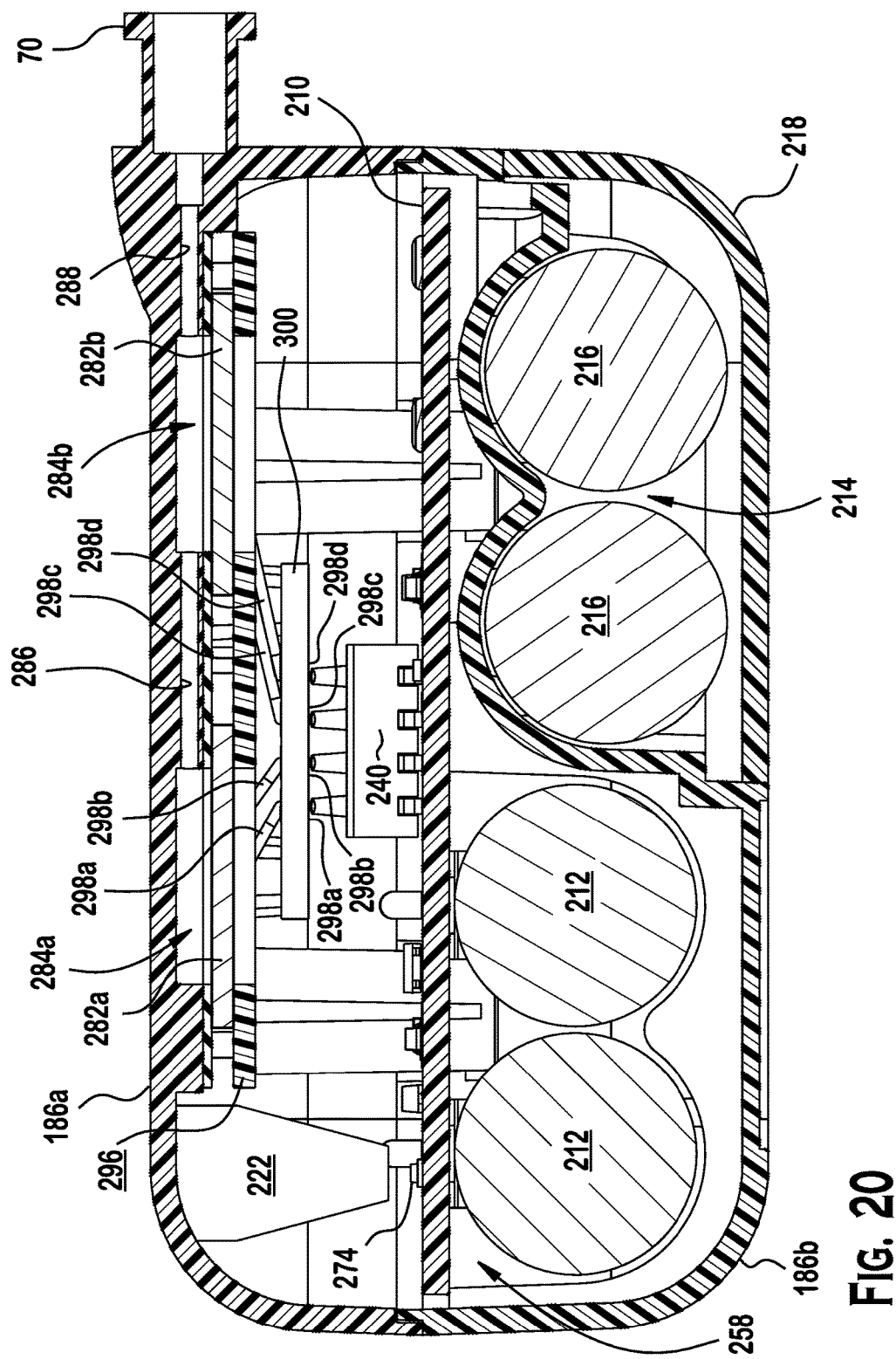
FIG. 20 is a cross-sectional view of the wound care device of FIG. 11, along line 20-20.

As shown in FIG. 20, the electrical contacts 298a, 298b, 298c, 298d on the landing pad 300 are situated above the spring loaded contact assembly 240. When the front enclosure section 186a and the rear enclosure section 186b are joined, the electrical contacts 298a, 298b, 298c, 298d on the landing pad 300 are pressed against the respective contacts on the spring loaded contact assembly 240 to electrically connect the MEAs 282a, 282b to electrical circuitry on the PCB 210.

Figure 21:
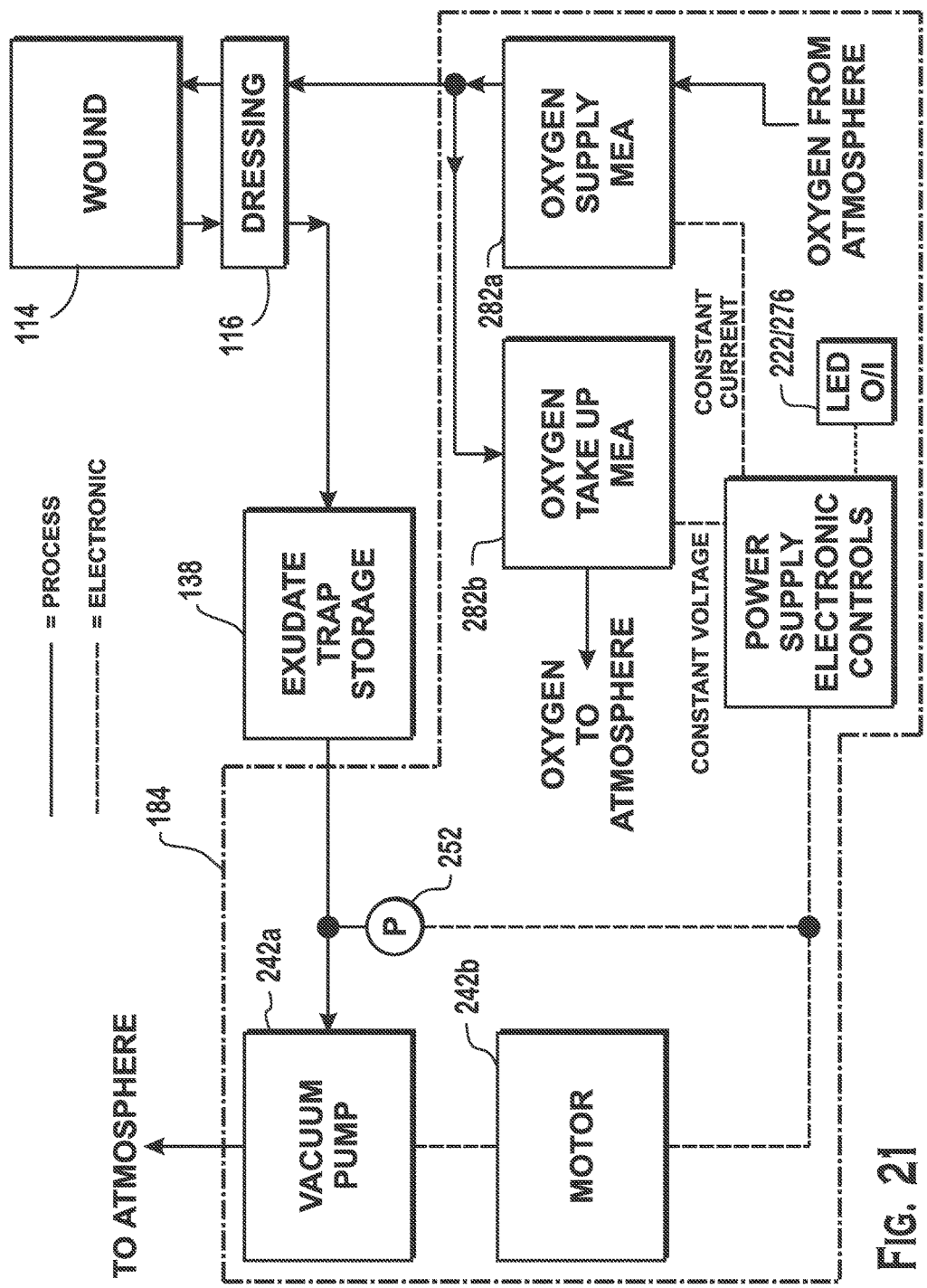
FIG. 21 is a block diagram of an exemplary wound care apparatus including the wound care device of FIG. 11, an exemplary dressing for applying wound care therapies to a wound, and an external container for trapping and storing wound exudates.

Referring to FIG. 21, the wound care device 184 may include an oxygen supply MEA 282a, an oxygen consuming MEA 282b, a vacuum pump and motor 242a, 242b, a pressure sensor 252, a power supply and electronic controls, LEDs 222, and input/output devices 276. A dressing 116 may be connected to the wound care device 184 to provide treatment for a wound 114. A canister (or exudate trap) 138 may be positioned between the dressing and the vacuum supply port of the vacuum pump to collect and store exudates from the wound. The canister may be combined with the dressing 136 as shown in FIG. 6. A pressure sensor 252 may be positioned at the vacuum supply port. The pressure sensor 252 may be part of the control circuitry that regulates the operation of the wound care device. For example, the pressure sensor 252 may be used by a control circuit to monitor the pressure applied to the dressing and to adjust (or control) operation of the vacuum pump 242a to maintain a desired therapeutic vacuum level inside the dressing (e.g., 80-100 mmHg). Operation of the vacuum 242a pump may be regulated by the control circuit, as well as by duty cycle requirements as determined by any local process controls. The oxygen supply MEA 282a may be operated by a circuit that provides a constant current across the membrane electrodes. By contrast, the oxygen consuming MEA 282b may be operated by a circuit that provides constant voltage across the MEA electrodes. The power supply may include independent sources and circuits for the vacuum pump motor 242b and the MEAs 282a, 282b. The power supply for the control circuit that may regulate operation of the wound care device as a whole may be independent, as well. Still, the power supply for the control circuit may be derived from one of the other two power supplies. The status indicator LEDs 222 and any other input/output devices may be connected to the control circuit as well. Preferably, the control circuit will include a microcontroller 238 that has been pre-loaded with firmware to regulate operation of the wound care device. Thus, the device 184 may be loaded with a standard firmware program for one of a number of wound care therapies. Still, the firmware may be updateable. Accordingly, a patient specific modality of treatment may be prescribed by a doctor and loaded into the device.

Figure 22:
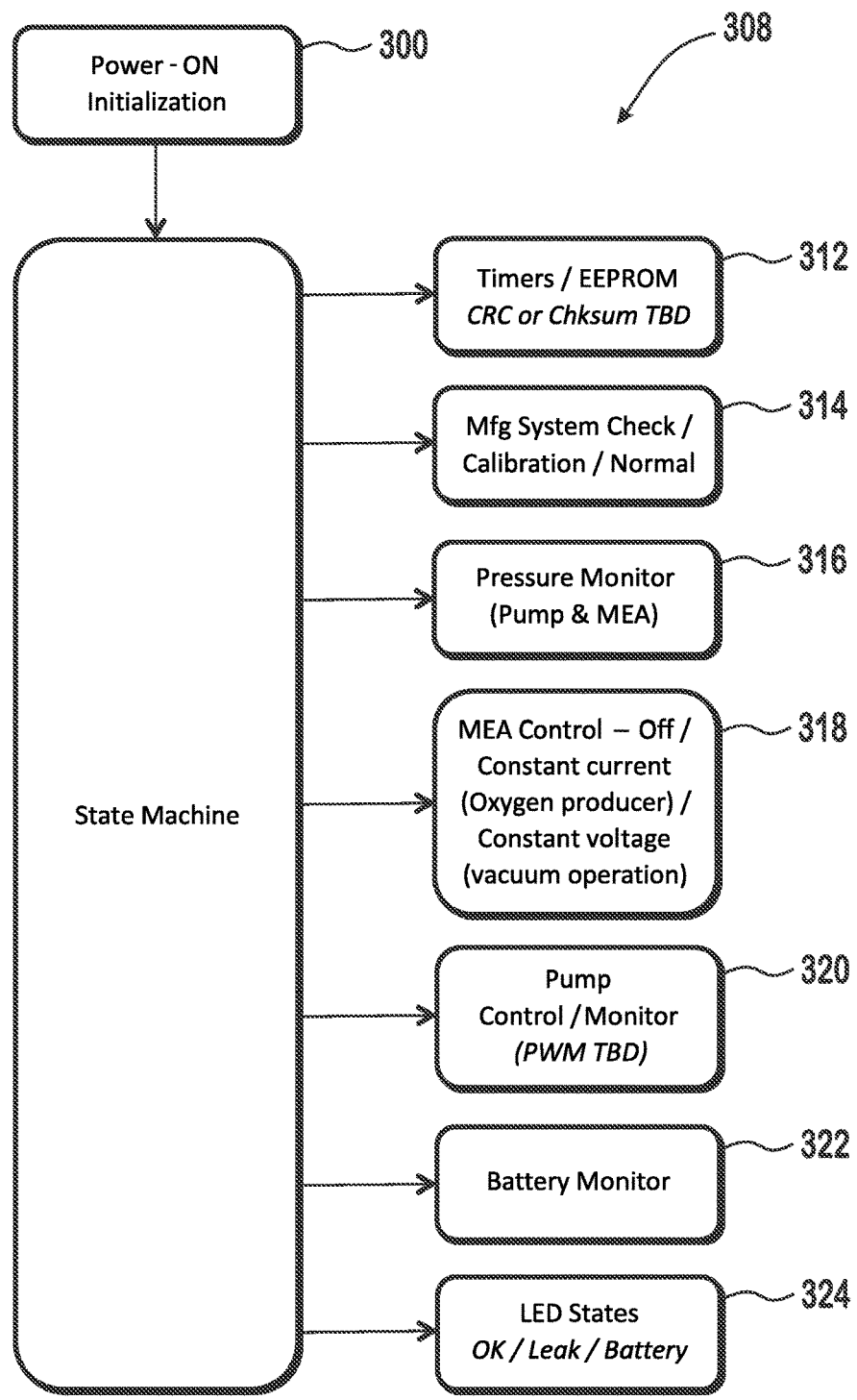
FIG. 22 is schematic overview of an exemplary embodiment of software architecture for electronically controlling operation of the wound care device of FIG. 11.

Referring to FIG. 22, the exemplary software architecture overview 308 for regulating operation of the wound care device 184 may include the following configuration. The wound care device 184 may be turned on by closing a mechanical switch. The wound care device may then power on 300 and activate a state machine. The state machine may be a microcontroller. During a typical cycle of the state machine, the state machine may connect with the following components: a timer 312, a manufacturer system check 314, a pressure monitor 316, an MEA control 318, a vacuum pump control/monitor 320, a battery monitor 322, and LED states 324. For example:

1. A timer may be initiated at startup and may be updated during each cycle of the state machine. If the wound care device has been operating for seven days, the microcontroller may disable the device. The timer may track "on" time in blocks of time. For example, without limitation, each block of time may be 10 minutes.
2. A manufacturer system check may be initiated at startup and may be updated during each cycle of the state machine. The manufacturer system check would verify operation of system components (e.g., the MEAs and vacuum pump) and then light the appropriate LED based on the status of the check.
3. A pressure monitor check may be initiated at startup and may be updated during each cycle of the state machine. The pressure sensor may be positioned near the vacuum pump intake or the MEA oxygen supply outlet. If the wound care device is operating properly, the measured value at these two locations should be related and close in value. Alternatively, the pressure monitor check may monitor the pressure near the vacuum pump intake and the MEA oxygen supply outlet.
4. MEA control may regulate operation of the MEAs. The two MEAs may be off (or non-operational), in an oxygen generation mode in which one MEA operates on constant current, or in an oxygen consuming mode in which the other MEA operates on constant voltage.
5. Pump control may regulate operation of the vacuum pump via the motor. The pump may be off (or non-operational), or on but subject to duty cycle limitations. The pump may be controlled using a pulse width modulation voltage supply. The pump operation may be regulated to provide a target pressure of between 80-100 mmHg vacuum at the vacuum pump inlet.
6. The battery voltage of each power supply may be monitored. If the voltage of the replaceable batteries falls below a certain level, an LED warning light may be lit.
7. LEDs may be lit to reflect the operating status of the wound care device.

Figure 23A:
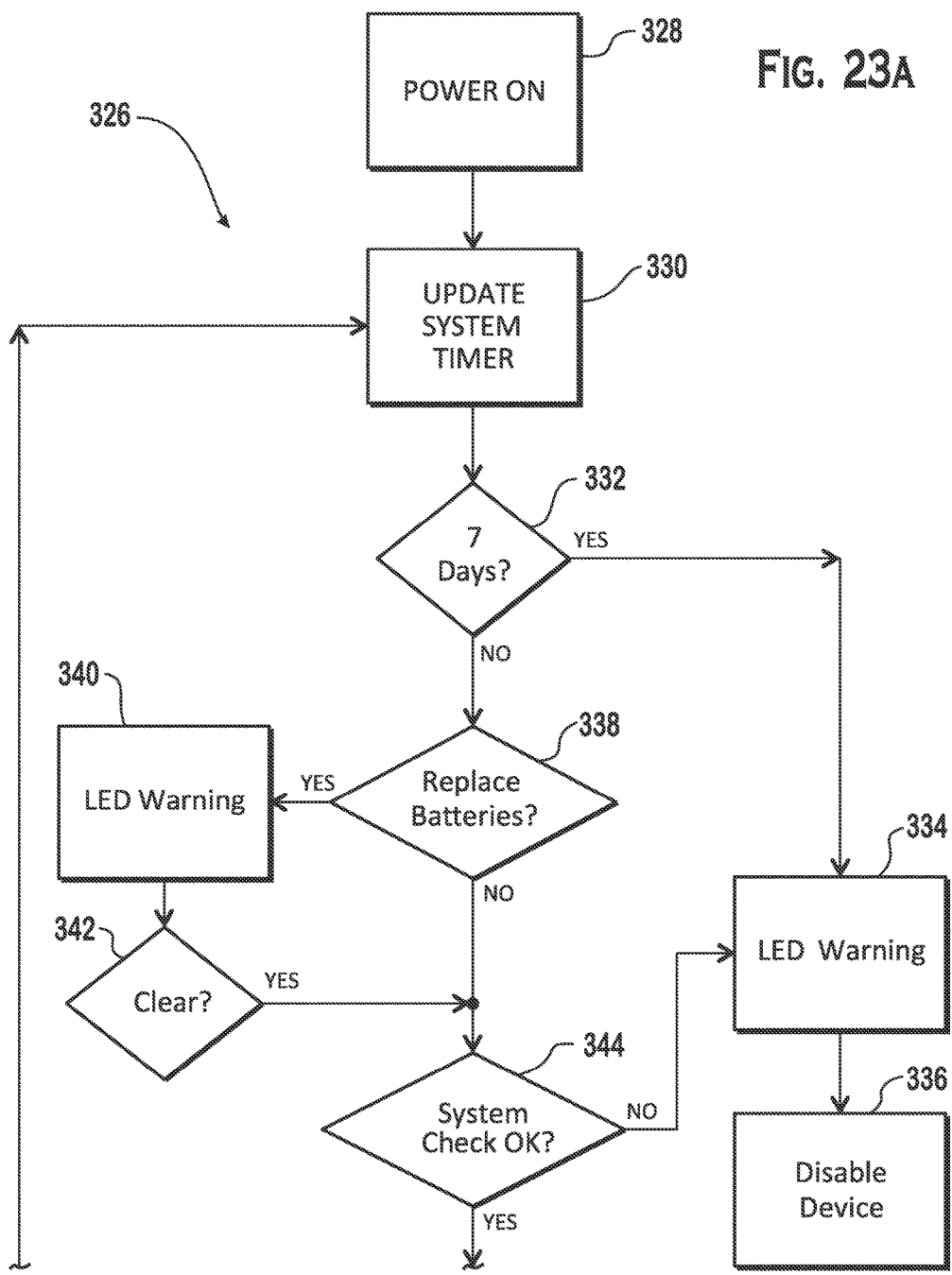
FIG. 23A is the first of two portions of an exemplary flow diagram of a first treatment mode of the wound care device of FIG. 11.
Figure 23B:
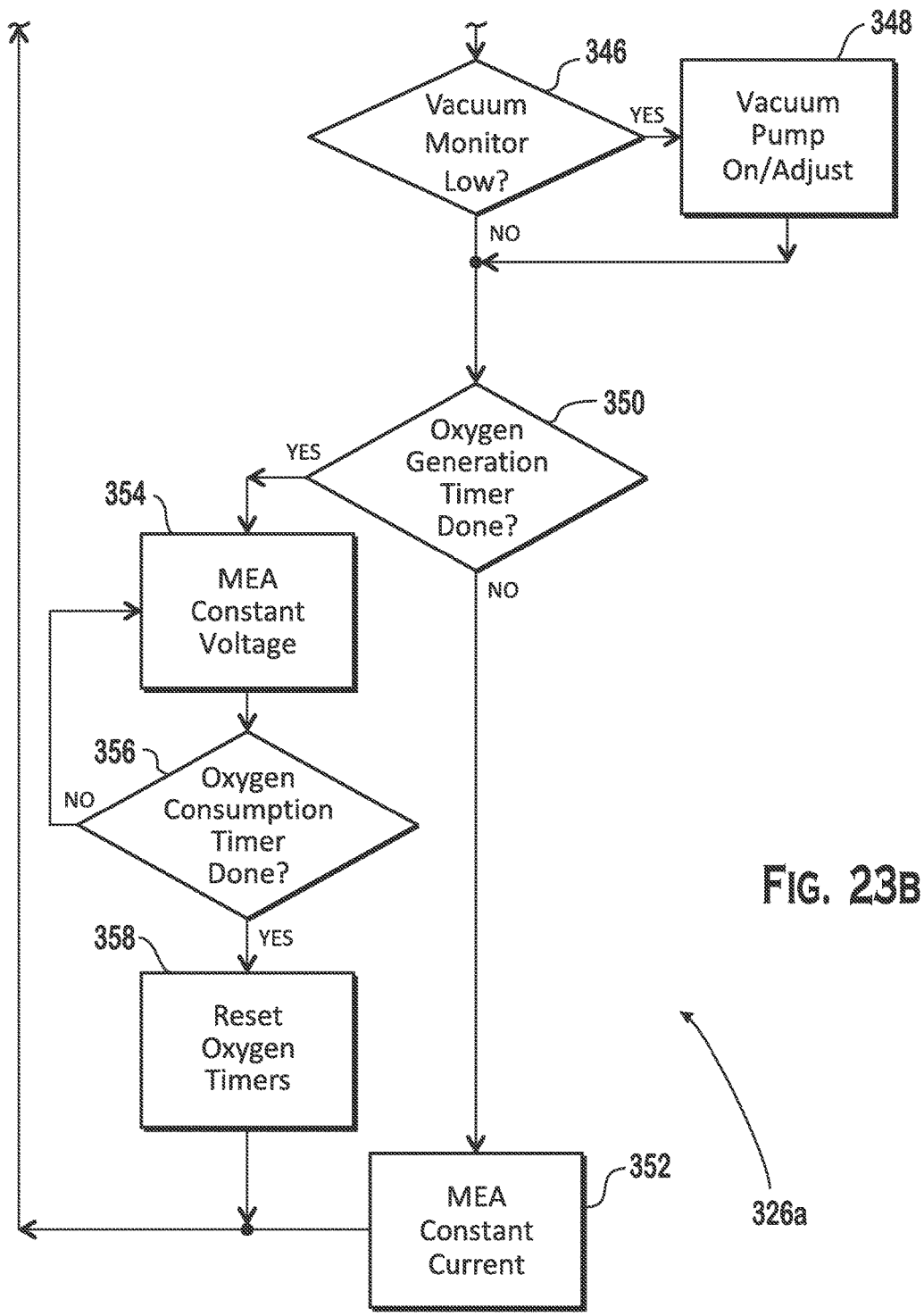
FIG. 23B is the second of two portions of the exemplary flow diagram of FIG. 23A.

FIG. 23A and FIG. 23B show a schematic flow chart 326 for an exemplary TCOT and NPWT treatment mode that may be used to regulate operation of the wound care device. The treatment mode may start when the wound care device is powered on 328. The system timer may be updated 330, and the value of the system timer may be compared to a pre-set value 332 that determines the duration of the treatment cycle. In FIG. 23A the duration of the treatment cycle is seven days. If the value of the system timer is seven days or more, than an LED warning 334 is given to provide a visual signal that the treatment cycle has been completed. The wound care device then may be disabled 336. By contrast, if the value system timer is less than seven days, then the replaceable power supply is evaluated 338 to determine whether the batteries should be replaced. For example, the voltage of the replaceable power supply may be measured and if the measured value of the replaceable power supply voltage is less than a pre-set value, then an LED warning 340 is given to provide a visual signal that the batteries in the replaceable power supply compartment should be replaced. The visual signal may be cleared 342 by replacing the batteries in the replaceable power supply. After the LED warning 340 has been cleared 342 or if the batteries did not need to be replaced, then a system check 344 may be undertaken. If the system check 344 determines that the system is not OK (e.g., has not passed the required system checks), then an LED warning 334 is given to provide a visual signal that the system is not OK. The wound care device then may be disabled 336. If, however, the system check 344 determines that the system is OK (e.g., has passed the required system checks), then wound treatment processes may be monitored and regulated.

Referring to FIG. 23B, the monitoring and regulation of wound treatment processes may start with an evaluation of the pressure 346 of the dressing headspace, which may be measured in the vacuum line, at the wound site, or in the oxygen delivery line. If the measured pressure is higher than the desired range, then the vacuum pump is turned on. For example, the pressure measurement may be collected from a pressure sensor in the vacuum line at (or near) the vacuum pump intake. If the pressure measurement indicates that the vacuum level in the dressing is not low, then no action is taken with the pump. After assessing and/or regulating the operation of the vacuum pump, the treatment program may assess and/or regulate operation of the MEAs.

An oxygen generation timer may be pre-set to a value $T_{OG}$ that determines the duration of oxygen generation in a dual action treatment sub-cycle. The oxygen generation timer may be evaluated to determine whether the oxygen generation timer is done 350. If the oxygen generation timer has not expired, then one MEA may be operated in a constant current setting 352 to concentrate oxygen for delivery to the dressing; whereas, the other MEA may be off. The system timer may be updated 330 and the subroutine continued. By contrast, if the oxygen generation timer has expired, then the other MEA may be operated in a constant voltage setting 354 to consume oxygen from the dressing. The other MEA may be operated in a constant voltage setting until an oxygen consumption timer expires 356. The oxygen consumption timer may be pre-set to a value $T_{OC}$ that determines the duration of oxygen consumption in the dual action sub-cycle (DASC). After the oxygen consumption timer expires, the oxygen generation timer and the oxygen consumption timer may be reset 358. Then the system timer 330 may be updated, and the subroutine continued.

Figure 25:
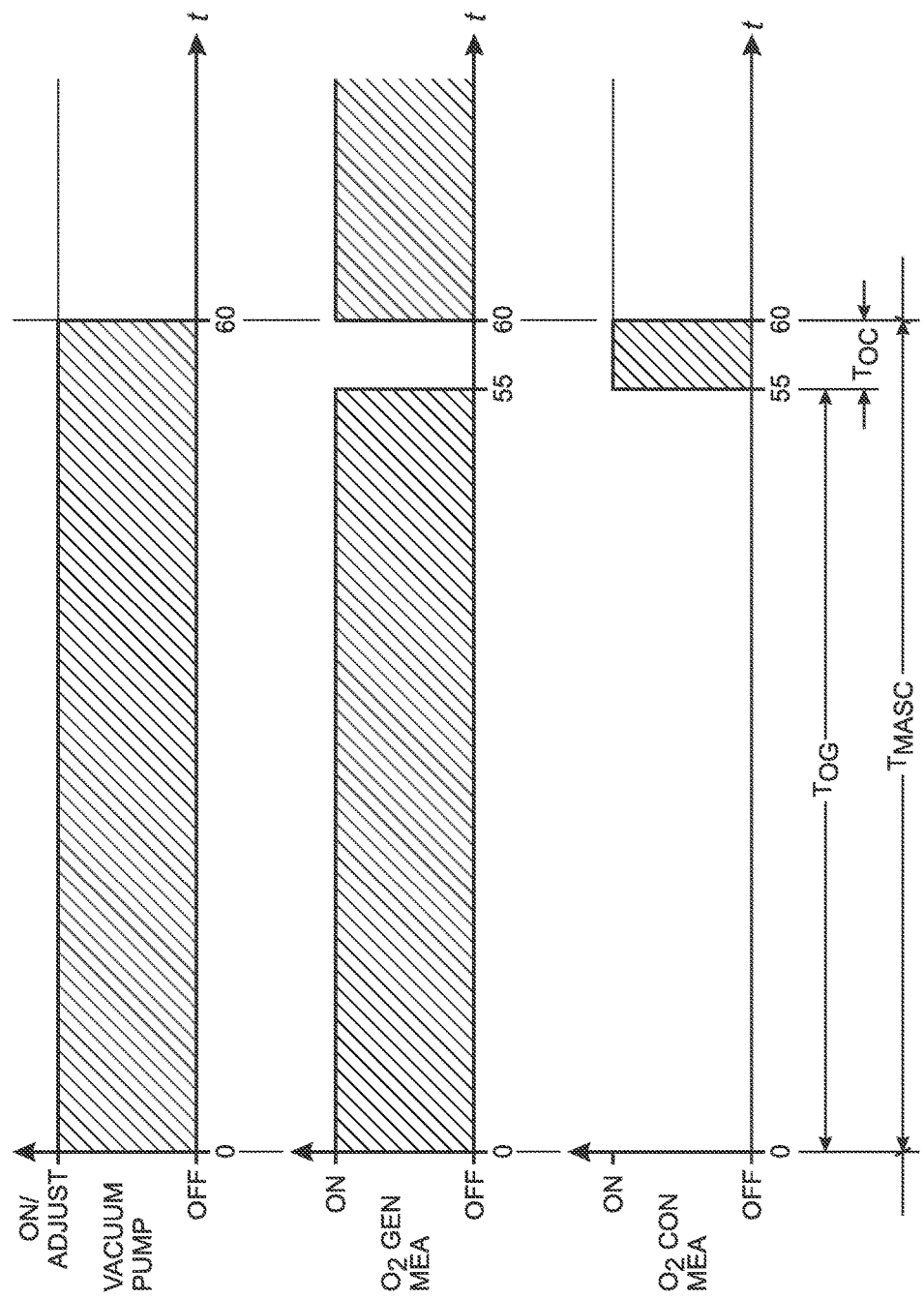
FIG. 25 is a schematic diagram of primary unit process operations for an exemplary therapy cycle in accordance with the first treatment mode of FIG. 23A and FIG. 23B.

FIG. 25 depicts the operating state of the vacuum pump, oxygen generating MEA, and oxygen consuming MEA for an exemplary TCOT and NPWT dual action sub-cycle in accordance with the schematic flow chart of FIG. 23A and FIG. 23B, where the oxygen generation timer value $T_{OG}$ is set to a value of 55 minutes and the oxygen consumption timer value is set to a value of 5 minutes. The exemplary TCOT and NPWT dual action sub-cycle would be completed every hour for the duration of the treatment cycle, which in this example is seven days.

Figure 24B:
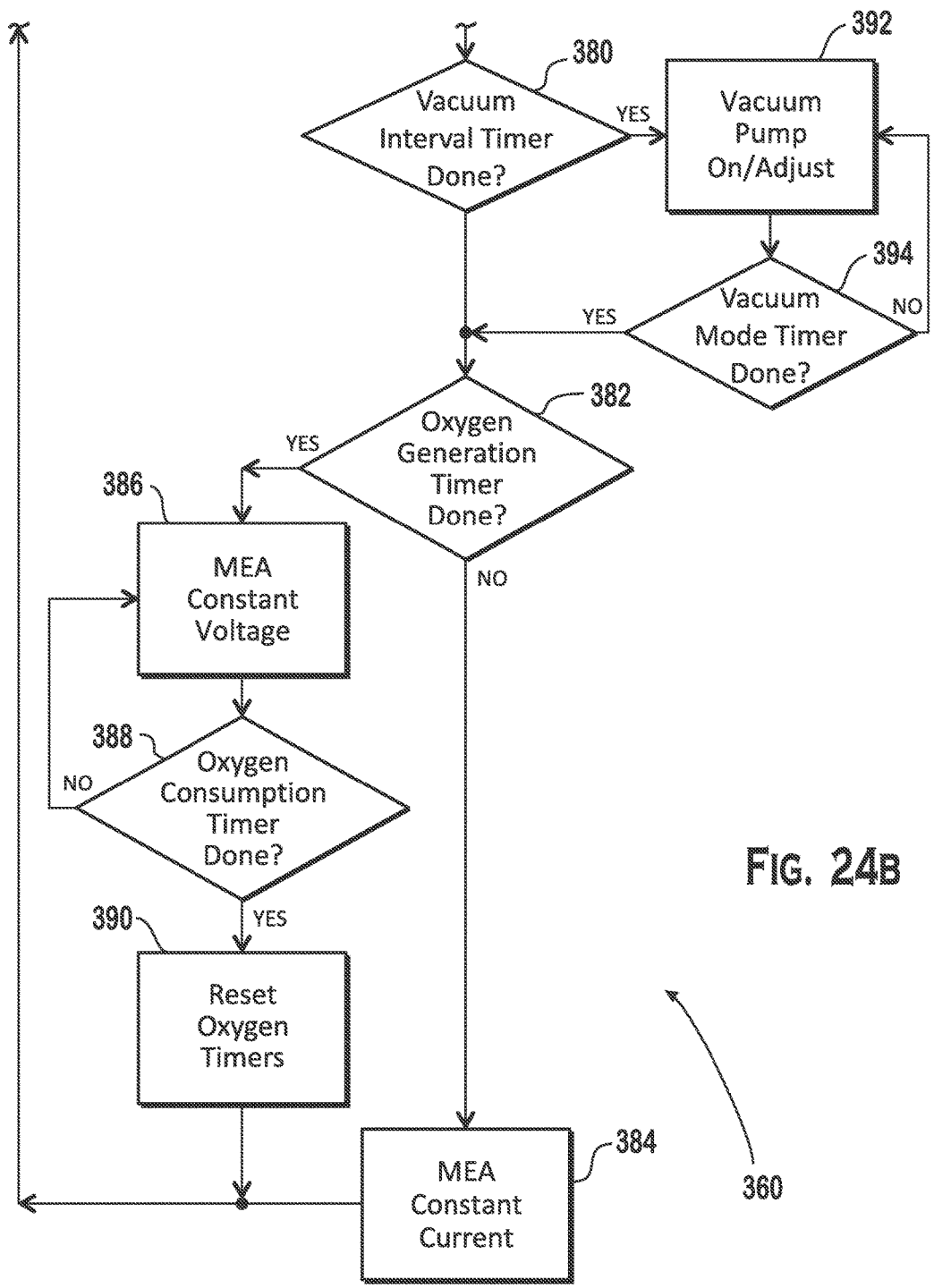
FIG. 24B is the second of two portions of the exemplary flow diagram of FIG. 24A.

FIG. 24A and FIG. 24B show a schematic flow chart for an exemplary TCOT and intermittent NPWT treatment mode that may be used to regulate operation of the wound care device. The treatment mode may start when the wound care device is powered on 362. The system timer may be updated 364, and the value of the system timer may be compared 366 to a pre-set value that determines the duration of the treatment cycle. In FIG. 24A the duration of the treatment cycle is seven days. If the value of the system timer is seven days or more, then an LED warning 376 is given to provide a visual signal that the treatment cycle has been completed. The wound care device 184 may then be disabled. By contrast, if the value system timer is less than seven days, then the replaceable power supply is evaluated 370 to determine whether the batteries should be replaced. For example, the voltage of the replaceable power supply may be measured and if the measured value of the replaceable power supply voltage is less than a pre-set value, then an LED warning 368 is given to provide a visual signal that the batteries in the replaceable power supply compartment should be replaced. The visual signal may be cleared 372 by replacing the batteries in the replaceable power supply. After the LED warning 368 has been cleared, or if the batteries did not need to be replaced, a system check may be undertaken 374. If the system check 374 determines that the system is not OK (e.g., has not passed the required system checks), then an LED warning 376 is given to provide a visual signal that the system is not OK. The wound care device 184 may then be disabled 378. If, however, the system check 374 determines that the system is OK (e.g., has passed the required system checks), then wound treatment processes may be monitored and regulated.

Referring to FIG. 24B, a vacuum interval timer may be pre-set to a value $T_{VINT}$ that determines the interval between the start of the MEA assembly dual action sub-cycle (DASC) and the start of NPWT. Additionally, a vacuum mode timer may be pre-set to a value $T_{VAC}$ that determines the duration of NPWT in this exemplary prescribed therapeutic sub-cycle (PTSC).

The vacuum interval timer may be evaluated to determine whether the vacuum interval timer has expired 380. If the vacuum interval timer has not expired and the oxygen generation timer has not expired 382 then one MEA may be operated in a constant current setting 384 to concentrate oxygen for delivery to the dressing. The system timer may be updated 364 and the subroutine continued. On the other hand, if the vacuum interval timer has not expired 380, but the oxygen generation timer has expired 382, then the other MEA may be operated in a constant voltage setting 386 to consume oxygen from the dressing. The other MEA may be operated in a constant voltage setting until an oxygen consumption timer expires 388. The oxygen consumption timer may be pre-set to a value $T_{OC}$ that determines the duration of oxygen consumption in the MEA assembly sub-cycle (MASC). After the oxygen consumption timer expires, the oxygen generation timer and the oxygen consumption timer may be reset 390. Then the system timer may be updated 364, and the subroutine continued.

If the vacuum interval timer has expired 380, however, the monitoring and regulation of wound treatment processes may start with an evaluation of the pressure of the dressing headspace, which may be measured in the vacuum line, at the wound site, or oxygen delivery line. If the measured pressure is higher than the desired range, the vacuum pump is turned on 392. For example, the pressure measurement may be collected from a pressure sensor in the vacuum line at (or near) the vacuum pump intake. If the pressure measurement indicates that the vacuum level in the dressing is not low, then no action is taken with the pump. The monitoring and regulation of the vacuum pump operation may continue until the vacuum mode timer expires 394. After the vacuum mode timer expires 394 the oxygen timers are reset 390, as the oxygen generation timer 382 has expired and the oxygen consumption timer 388 has expired. Then the system timer 364 may be updated, and the subroutine continued.

Figure 26:
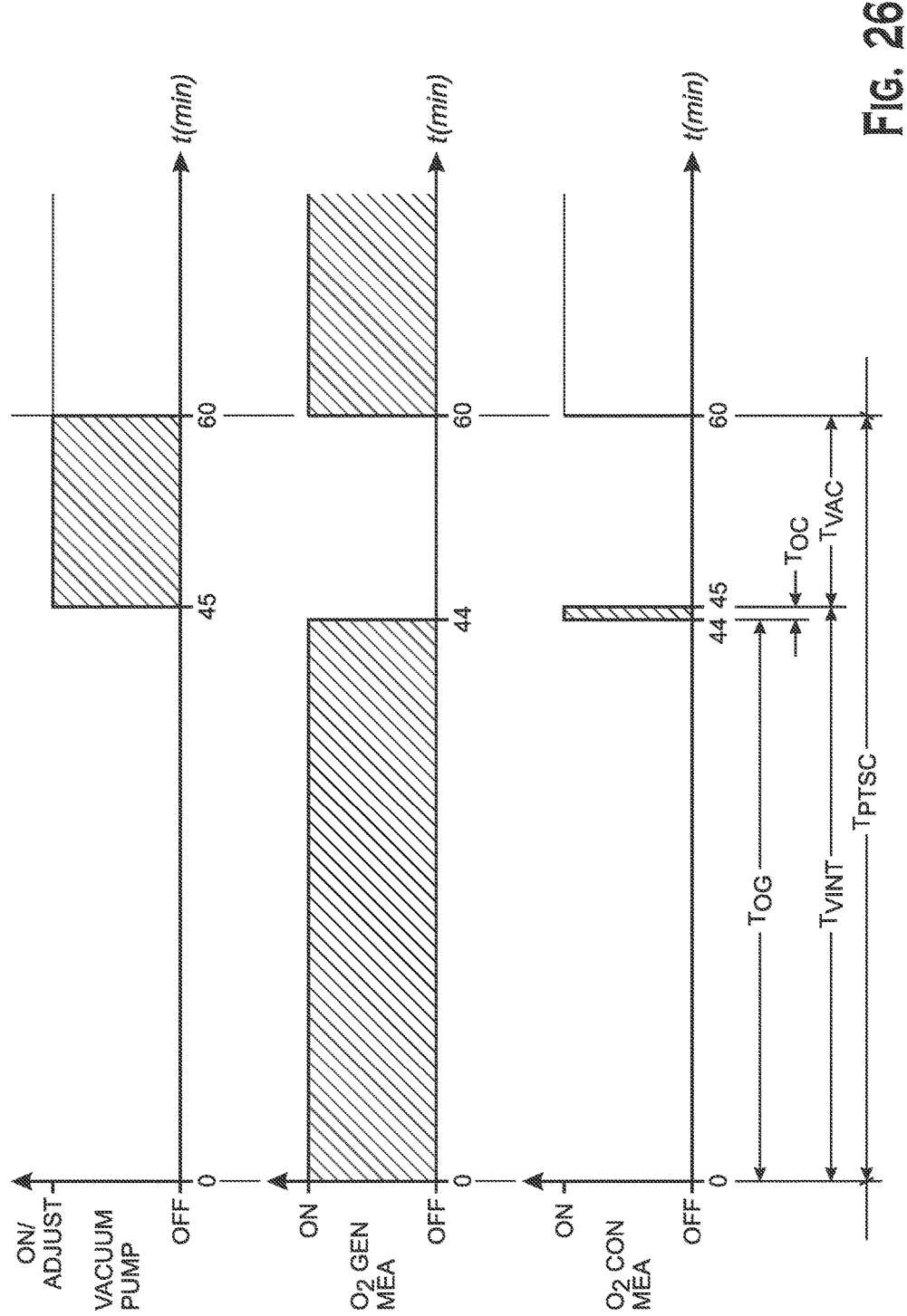
FIG. 26 is a schematic diagram of primary unit process operations for an exemplary therapy cycle in accordance with the second treatment mode of FIG. 24A and FIG. 24B.

FIG. 26 depicts the operating state of the vacuum pump, oxygen generating MEA, and oxygen consuming MEA for an exemplary TCOT and intermittent NPWT sub-cycle in accordance with the schematic flow chart of FIG. 24A and FIG. 24B, where the oxygen generation timer value $T_{OG}$ is set to a value of 44 minutes, the oxygen consumption timer value is set to a value of 1 minute, the vacuum interval timer is set to a value of 45 minutes, and the vacuum mode timer is set to 15 minutes. This exemplary prescribed therapy sub-cycle would be completed every hour for the duration of the treatment cycle, which in this example is seven days.

In use, the foregoing devices and dressings may be combined to form an apparatus that may be used to provide negative pressure wound therapy and transdermal oxygen therapy to a wound. The apparatus may include a treatment device which houses an MEA oxygen concentrator and the mechanical pump for delivering negative pressure, as well as a dressing that includes inlet and outlet connections terminating in a manifold to facilitate a substantially uniform flow of oxygen across the treatment area. The treatment devices may be disposable and may be designed for a single clinical use. For example, the treatment device may be designed to operate continuously for at least 7 days. In another example, the treatment device may be designed to operate continuously for at least 15 days. In another example, the treatment device may be designed to operate continuously for at least 30 days. And, in yet another example, the treatment device may be designed to operate continuously for at least 60 days. The dressings and tubing may be adapted for use specifically with the treatment device(s). As these consumables may be replaced on an as needed basis, the dressing(s) and tubing may be available in individually sealed sterile packaging.

Generally, treatment of a wound involving negative pressure wound therapy and transdermal oxygen therapy may be ordered by a physician. After the wound is inspected, cleansed and otherwise appropriately prepared for treatment, the dressing may be placed in the wound and the surrounding area may be covered with the semi-occlusive layer. Two openings may be created in the semi-occlusive layer above the dressing's vacuum and oxygen supply manifolds, respectively. The tubing associated with each manifold then may be passed through the respective openings. Alternatively, the dressing and semi-occlusive layer may be provided in an integral configuration. Sealant may be used to provide an airtight seal around the tube penetrations in the semi-occlusive layer. The oxygen supply tubing may be connected to the oxygen port of the device. The vacuum supply tubing may be connected to the vacuum port of the device.

The treatment device may be powered on by depressing (or otherwise activating) the power button. The device may undergo a start-up process that includes a diagnostic assessment which confirms that the device is operating properly, that the apparatus does not include a leak or blockage, and that the differential pressure between the oxygen supply and vacuum supply is in the expected range of a fresh dressing. The results of the diagnostic assessment may be reported to the status indicators and any correction of any identified adverse conditions may be required before a treatment operation may commence.

During treatment, the MEA may be operational ("on") or nonoperational ("off"). When the MEA is on and in a first operational mode, the MEA may be concentrating atmospheric oxygen for delivery to the oxygen supply port at a rate ranging from approximately 1 cc/hr to approximately 100 cc/hr. The concentrated oxygen, which may be nearly pure, may be delivered to the dressing and wound environment. By contrast, when the MEA is on and in a second operational mode, the MEA may be consuming oxygen from the dressing headspace at a very rapid rate (e.g. a rate ranging from about 5 to about 50 times greater than the respective oxygen generation rate of the MEA under normal operating conditions). Generally, the oxygen consumption rate of the MEA may be related to the current delivering capability of the power supply and the amount of oxygen available for consumption. In view of the above, consumption of oxygen by the MEA may result in the application of a vacuum to the dressing and wound site. The vacuum applied by the MEA to the wound site may range from approximately 1 mmHg to approximately 50 mmHg.

Additionally, the mechanical pump may be operational ("on") or nonoperational ("off"). When the mechanical pump is on and in a third operational mode, the mechanical pump may evacuate waste gas and liquid exudate at a rate in the range of approximately 1 cc/min to approximately 2,500 cc/min. The pressure at the dressing manifold may range from approximately 560 mmHg to approximately 680 mmHg.

The treatment devices may initiate a first treatment modality in which one MEA is in the first operational mode and the mechanical pump is in the third operational mode. For example, the MEA may supply oxygen to the dressing at a rate of approximately 3 cc/hr and the mechanical pump may be operationally controlled to apply a vacuum of approximately 100 mmHg to the dressing and an average throughput (or flow rate) of approximately 1 cc/hr. The balance of the supplied oxygen (i.e., 2 cc/hr) may be consumed by the wound and adjacent skin. In the first operational mode, the supply of oxygen is controlled by the amount of current passing between the MEA electrodes. In the third operational mode, the applied vacuum may be set by the pump speed which may be controlled through pulse width modulation. Alternatively, the pump speed may operate at a set point and the pump operation may be regulated with a microprocessor controlled power switch capable of regulating the "on" and "off" timing intervals according to the programmed values. Accordingly, the first treatment modality may apply NPWT and transdermal oxygen therapy to the wound.

Treatment administered using the devices of FIG. 1 or FIG. 9 may initiate a second treatment modality with the MEA in the second operational mode and the mechanical pump on standby. In the second treatment modality, the polarity of the MEA may be switched, and a constant voltage may be applied across the MEA electrodes. By contrast, treatment administered by the device of FIG. 10 and FIG. 11 may include an MEA dedicated to supplying negative pressure to the wound. Accordingly, the second treatment modality may apply lower levels of suction to the wound than applied during NPWT.

The treatment devices may initiate a third treatment modality with an oxygen concentrating MEA in the first operational mode and the mechanical pump on standby. Accordingly, the third treatment modality may apply transdermal oxygen therapy to the wound.

The treatment devices may initiate a fourth treatment modality with an oxygen concentrating MEA in standby and the mechanical pump in the third operational mode. Accordingly, the fourth treatment modality may apply NPWT to the wound.

The foregoing treatment modalities may be combined into sequences of treatment (or therapies). The sequence of treatment modalities applied by the devices to a wound may be programmed into the functionality of the device and manually set or implemented by a user of the device. Accordingly, the device may allow for the application of a wide combination of therapies for treating wounds in a mobile device that may be adapted to the therapeutic and clinical needs of the patient.

While it has been illustrated and described what at present is considered to be a preferred embodiment(s) of the present invention, it will be understood by those skilled in the art that various changes and modifications may be made, and equivalents may be substituted for elements thereof without departing from the true scope of the invention. For example, in some treatment therapies where the vacuum pump and the oxygen consuming MEA do not operate at the same time, the oxygen consuming MEA may be connected to the vacuum port and segregated from the oxygen generating MEA. Additionally, features and/or elements from any embodiment may be used singly or in combination with other embodiments. Therefore, it is intended that this invention not be limited to the particular embodiments disclosed herein, but that the invention include all embodiments falling within the scope and the spirit of the present invention.

What is claimed is:

1. A wound care device comprising:
    an oxygen port for supplying oxygen gas for wound care;
    an oxygen concentrating device fluidly connected to the oxygen port, the oxygen concentrating device including:
    a first membrane electrode assembly (MEA) for the production of oxygen gas from air, which comprises:
        a first electrode fluidly connected to a source of ambient air;
        a cover disposed between the first electrode and the source of ambient air, the cover including at least one passage which fluidly connects the first electrode to the source of ambient air such that the cover restricts moisture loss from the first electrode, a second electrode spaced from the first electrode, the second electrode being fluidly connected to a first basin such that the first basin is fluidly connected to the oxygen port, and a first ion conducting membrane positioned between the first and second electrodes, which comprises:

a first conductive wire connected to the first electrode, and a second conductive wire connected to the second electrode, such that the application of a substantially constant flow of electrical current through the first conductive wire and the second conductive wire electrochemically produces oxygen on the second electrode from ambient air adjacent the first electrode, and such that when the source of ambient air has an ambient relative humidity which is equal to or less than 30%, the voltage across the first electrode and the second electrode increases less than 25% after 15 days of electrochemically producing oxygen on the second electrode as the result of the application of the substantially constant flow of electrical current;

wherein the at least one passage has a radius that is equal to or greater than 0.159 mm.

2. The device of claim 1, further comprising:
a vacuum port for providing a vacuum for wound care; and
a mechanical pump which comprises:
a pump intake fluidly connected to the vacuum port, and
a motor for driving the mechanical pump such that the motor drives the mechanical pump to evacuate a gaseous mixture at a temperature ranging from 60° F. to 100° F. and a pressure ranging from 560 mmHg absolute to 760 mmHg absolute at a volumetric flow rate ranging from 1 cc/min to 2,500 cc/min while maintaining a vacuum at the pump intake, the vacuum ranging from 100 mmHg to 500 mmHg.

3. The device of claim 2, further comprising an oxygen consuming device fluidly connected to the oxygen port, the oxygen consuming device comprises:
a second MEA for the removal of oxygen from a gaseous mixture, which comprises:
a third electrode fluidly connected to the first basin,
a fourth electrode spaced from the third electrode,
a second ion conducting membrane positioned between the third and fourth electrodes,
a third conductive wire connected to the third electrode, and
a fourth conductive wire connected to the fourth electrode, such that the application of a constant voltage across the third conductive wire and the fourth conductive wire electrochemically consumes oxygen from the first basin at the third electrode.

4. The device of claim 3, further comprising a pressure sensor and a microcontroller electrically connected to the first MEA, the second MEA, the motor, and the pressure sensor, the microcontroller being configured to regulate operation of the wound care device in a plurality of operational modes which comprise:
a first operational mode in which the first MEA delivers oxygen gas to the oxygen port at a rate ranging from 1 ml oxygen/hr to 10 ml oxygen/hr at a temperature ranging from 60° F. to 100° F. and a pressure of 760 mmHg; and
a second operational mode in which the second MEA consumes oxygen from the oxygen port, and a third operational mode in which the mechanical pump evacuates a gaseous mixture from the vacuum port at a volumetric flow rate ranging from 1 cc/min to 2,500 cc/min while maintaining a pressure ranging from 560 mmHg to 680 mmHg at a wound site which is fluidly connected to the vacuum port.

5. The device of claim 4, wherein the microcontroller regulates simultaneous operation of the first operational mode and the third operational mode.

6. The device of claim 4, wherein the microcontroller regulates operation of the second operational mode after regulating operation of the first operational mode.

7. The device of claim 4, further comprising an enclosure for housing the first MEA, the second MEA, and the mechanical pump.

8. The device of claim 7, wherein the enclosure comprises a cover section and a base section.

9. The device of claim 8, wherein the first MEA and the second MEA are secured to the cover section.

10. The device of claim 9, wherein the mechanical pump is connected to the base section.

11. The device of claim 10, wherein the oxygen port is connected to the cover section and the vacuum port is connected to the base section.

12. The device of claim 8, wherein the first basin comprises a recess in the cover section.

13. The device of claim 12, further comprising a second basin adjacent the first basin.

14. The device of claim 13, further comprising an intermediate passage fluidly connecting the first basin and the second basin.

15. The device of claim 14, wherein the second basin is opposite the second MEA.

16. The device of claim 15, further comprising a plurality of LEDs connected to the microcontroller for signaling a status of one or more operating parameters.

17. The device of claim 16, wherein the device further comprises a replaceable power supply for operating the motor.

18. The device of claim 16, wherein the device further comprises a rechargeable power supply for operating the motor.

19. The device of claim 2, wherein the pressure sensor is fluidly connected to the vacuum port at a location between the mechanical pump and the vacuum port.

20. The device of claim 2, wherein the pressure sensor is fluidly connected to the oxygen port at a location between the first MEA and the oxygen port.

21. The device of claim 2, further comprising a trap for storing wound care exudates, the trap being fluidly connected to the pump intake.

22. The device of claim 1, wherein the at least one passage is a plurality of passages which fluidly connect the first electrode to the source of ambient air.

23. The device of claim 22, wherein the plurality of passages each have a cross-sectional area of approximately 0.01 cm$^2$.

24. The device of claim 22, wherein four passages fluidly connect the first electrode to the source of ambient air.

25. The device of claim 1, wherein the substantially constant flow of electrical current is approximately 13.5 mA.

26. An apparatus for treating a wound comprising:
a wound care device of claim 1, and
a dressing for administering treatment to a wound, the dressing comprising an oxygen delivery zone fluidly connected to the oxygen port.

27. An apparatus for treating a wound comprising:
a wound care device of claim 2; and
a dressing for administering treatment to a wound, the dressing comprising:
  an oxygen delivery zone fluidly connected to the oxygen port, and
  a gaseous mixture and exudates removal zone fluidly connected to the vacuum port.

28. The apparatus of claim 27, further comprising a trap for storing wound care exudates, the trap being fluidly connected to the gaseous mixture and exudates removal zone and the pump intake, and the trap is located between the pump intake and the vacuum port.

29. The apparatus of claim 27, further comprising a trap for storing wound care exudates, the trap being fluidly connected to the gaseous mixture and exudates removal zone and the pump intake, and the trap is located in the dressing.

30. The apparatus of claim 27, further comprising a trap for storing wound care exudates, the trap being fluidly connected to the gaseous mixture and exudates removal zone and the pump intake, the trap including a container that is located between the vacuum port and the dressing.

31. A method of treating a wound comprising:
providing a wound care device of claim 2;
positioning a dressing over a wound to form a wound care environment for administering topical continuous oxygen therapy and negative pressure wound therapy;
connecting the dressing to the wound care device;
activating operation of the wound care device;
supplying oxygen concentrated by the wound care device to the wound care environment via the dressing; and
applying a vacuum produced by the wound care device to the wound care environment via the dressing.

32. The method of claim 31, wherein activating operation of the wound care device initiates a seven-day treatment cycle that comprises simultaneous topical continuous oxygen therapy and negative pressure wound therapy.

33. The method of claim 31, wherein activating operation of the wound care device initiates a seven-day treatment cycle that comprises topical continuous oxygen therapy and intermittent negative pressure wound therapy.

* * * * *